United States Patent [19]

Dalie et al.

[11] Patent Number: 5,597,710
[45] Date of Patent: Jan. 28, 1997

[54] HUMANIZED MONOCLONAL ANTIBODIES AGAINST HUMAN INTERLEUKIN-4

[75] Inventors: Barbara Dalie, Berkeley Heights; Kenneth Miller, Cranford; Nicholas Murgolo, Millington; Stephen Tindall, Madison, all of N.J.

[73] Assignee: Schering Corporation, Kenilworth, N.J.

[21] Appl. No.: 208,886

[22] Filed: Mar. 10, 1994

[51] Int. Cl.$^6$ .......................... C07H 21/04; C07K 16/46; C12N 1/20; C12N 15/00
[52] U.S. Cl. .......................... 435/69.6; 435/70.1; 435/70.3; 435/71.1; 435/252.3; 435/320.1; 435/69.1; 435/327; 435/335; 435/365; 530/387.3; 530/324; 536/23.4; 536/23.5; 536/23.53; 935/11; 935/15; 935/23; 935/71; 935/70
[58] Field of Search .......................... 530/387.3, 387.2, 530/324; 435/69.1, 70.21, 172.1, 240.27, 240.2, 252.3, 70.1, 70.3, 71.1, 320.1; 536/23.53, 23.4, 23.5; 935/11, 15, 23, 70, 71

[56] References Cited

U.S. PATENT DOCUMENTS

| | | | |
|---|---|---|---|
| 4,642,334 | 2/1987 | Moore et al. | 530/387.3 |
| 4,731,237 | 3/1988 | Reagan et al. | 424/131.2 |
| 5,041,381 | 8/1991 | Abrams et al. | 435/240.27 |

FOREIGN PATENT DOCUMENTS

| | | |
|---|---|---|
| 0239400 | 9/1987 | European Pat. Off. . |
| 0314402 | 5/1989 | European Pat. Off. . |
| 91/17179 | 11/1991 | WIPO . |
| 93/17106 | 9/1992 | WIPO . |

OTHER PUBLICATIONS

The Genzyme Catalog, 1991, pp. 35–36, Interleukin 4.
Brennan et al., Science 229:81 (1985).
Casali et al., Science 234:476 (1986).
DeKruyff et al., J. Exp. Med. 170:1477 (1989).
Geysen et al., J. Immunol. Meth. 102:259 (1987).
Huston et al., Proc. Nat'l. Acad. Sci. (USA) 85:5879 (1988).
Jameson, Nature 341:465 (1989).
Kabat et al., *Sequences of Proteins of Immunological Interest*, 4th ed., U.S. Dept. of Health and Human Services, (1987), pp. vii–xliv.
Kohler et al., Eur. J. Immunol. 6:511 (1976).
Larrick et al., Bio/Technology 7:934 (1989).
Lewis et al., Gene 101:297 (1991).
Liu et al., Proc. Natl. Acad. Sci. USA 84:3439 (1987).
Lundell et al., J. Indust. Microbiol. 5:215 (1990).
Milstein, *Immunology Recognition & Response*, 1991, W. E. Paul, Ed., W. H. Freeman & Company, New York, pp. 124–134.
Miyajima et al., TIBS 17:378 (1992).
Queen et al., Proc. Natl. Acad. Sci. USA 86:10029 (1989).
Regenmortel, *Immunogenicity of Protein Antigens: Repertoire and Regulation*, 1987, E. Sercarz and J. Bersofsky, Eds., CRC Press, Inc. Boca Raton, Florida, pp. 21–28.
Riechmann et al., Nature 332:323 (1988).
Saiki et al., Science 239:487 (1988).
Saragovi et al., Science 253:792 (1991).
Schmitter et al., Mol. Immunol. 27:1029 (1990).
Shulman et al., Nature 276:269 (1978).
Zurawski et al., EMBO J. 8:2583 (1989).

*Primary Examiner*—Frank C. Eisenschenk
*Attorney, Agent, or Firm*—Norman C. Dulak; Cynthia L. Foulke

[57] ABSTRACT

Humanized monoclonal antibodies are provided which are specific for human IL-4 and have properties unexpectedly superior to other, previously available humanized antibodies. Also provided are nucleic acids which encode the heavy and light chain variable regions of such monoclonal antibodies or antigenic fragments thereof; anti-idiotypic antibodies; and methods for detecting, measuring and immunopurifying human IL-4, and for blocking or mimicking the biological activity of human IL-4.

12 Claims, 3 Drawing Sheets

FIG. 1

|       | CDR1         | CDR2              | CDR3              |
|-------|--------------|-------------------|-------------------|
| LAY   | GFTFSASAMS   | WKYEGNDKHYADSVN   | DAGPYVSPTFFAH     |
| 25D2  | S RSYW T     | SISIS DNTY P R    | P - Y F GHY DF    |
| h25D2H-1 | S RSYW T  | SISIS DNTY P R    | P - Y F GHY DF    |
| h25D2H-2 | S RSY     | SISIS DNTY P R    | P - Y F GHY DF    |
| h25D2H-3 | SYW T     | SISIS DNTY P      | P - Y F GHY DF    |
| h25D2H-4 | SYW T     | SISIS DNTY P      | P - Y F GHY DF    |
| h25D2H-5 | S RSY     | SISIS DNTY P      | P - Y F GHY DF    |

——— CDR Loop
═══ Overlap of CDR Loop and Kabat Region
● Kabat Region

HUMANIZED MONOCLONAL ANTIBODIES AGAINST HUMAN INTERLEUKIN-4

BACKGROUND OF THE INVENTION

Human interleukin-4 (IL-4) is a highly pleiotropic lymphokine which affects many different components of the immune system. It has T cell growth factor (TCGF) activity and B cell growth factor activity. It is capable of potentiating the TCGF activity of interleukin-2 (IL-2) and the colony forming activity of granulocyte-macrophage colony stimulating factor (GM-CSF). It also induces (a) the preferential production of $IgG_1$ and IgE, (b) the low affinity receptor for IgE (CD23), and (c) the expression of human leukocyte class II DR antigens.

These activities suggest several possible therapeutic uses for IL-4, e.g., as an anti-tumor agent [Tepper et al., Cell 57:503 (1989)], a potentiating agent for IL-2 anticancer therapy, as a potentiating agent for GM-CSF-stimulated bone marrow regeneration, or as an agent to treat bare lymphocyte syndrome [Touraine, Lancet, pgs. 319–321 (Feb. 7, 1981); Touraine et at., Human Immunology 2:147 (1981); and Sullivan et at., J. Clin. Invest. 76:75 (1985)]. IL-4 and IL-4 agonists are thus potentially useful therapeutic agents.

On the other hand, the IgE- and CD23-inducing activity of IL-4 may have important adverse consequences for persons suffering from allergic diseases. The availability of IL-4 antagonists could provide an alternative to the use of glucocorticoid steroids, which have many deleterious side effects, especially with prolonged usage [Goodman and Gillman, *The Pharmacological Basis of Therapeutics*, 6th Ed. (MacMillan Publishing Company, New York, 1980)].

Monoclonal antibodies specific for blocking human IL-4 biological activity provide a means for constructing agonists or antagonists by generating anti-idiotype antibodies (U.S. Pat. No. 4,731,237) or by mimotope screening [Geysen et al., J. Immunol. Meth. 102:259 (1987); PCT patent applications WO 86/00991 and WO 86/06487]. Because most monoclonal antibodies are of rodent cell origin, however, there is a possibility that they would be immunogenic if used therapeutically in a human being, particularly over a long period of time.

To avoid this possibility, it is desirable to have human antibodies, or "humanized" antibodies, against human IL-4. The preparation of humanized antibodies against IL-4 has in fact been disclosed in International Patent Application Publication No. WO 93/17106. The disclosed antibodies while useful, however, do not have binding affinities equal to that of the starting rodent monoclonal antibody upon which they were based.

It would be desirable to have a humanized antibody against human IL-4 which would possess a binding affinity comparable to that of the rodent antibody. It cannot be predicted from the present state of the art, however, whether or how such an antibody could be produced.

SUMMARY OF THE INVENTION

The present invention provides such a high-affinity monoclonal antibody, methods and compositions useful for the treatment of IL-4-related diseases, and intermediates for making such materials.

More particularly, this invention provides polypeptides comprising light or heavy chain variable regions of a humanized monoclonal antibody against human IL-4 which have amino acid sequences shown in SEQ ID NO: 70 and SEQ ID NO: 79, respectively, or subsequences of such sequences. In one embodiment, such polypeptides comprise a complete humanized monoclonal antibody. In other embodiments they comprise IL-4-binding and/or antigenic fragments of the humanized monoclonal antibody.

The present invention further provides isolated DNAs that encode polypeptides comprising light or heavy chain variable regions of a humanized monoclonal antibody against human IL-4 which have amino acid sequences shown in SEQ ID NO: 70 and SEQ ID NO: 79, respectively, or subsequences of such sequences.

The present invention also provides recombinant vectors and host cells comprising the foregoing DNAs, and methods for making the polypeptides comprising culturing such host cells under conditions in which the DNAs are expressed.

This invention still further provides IL-4-binding compositions, single-chain binding proteins, fusion proteins and antibody fragments based on the humanized antibody.

Antibodies against the humanized antibody including anti-idiotypic antibodies, and fragments of such antibodies, are also provided by this invention, as are pharmaceutical compositions comprising a pharmaceutically acceptable carrier and one or more of the foregoing binding compositions, proteins, polypeptides, antigenic fragments, antibodies or antibody fragments.

BRIEF DESCRIPTION OF THE FIGURES

This invention can be more readily understood by reference to the accompanying Figures, in which:

FIG. 1 shows amino acid residue replacements made in various humanized antibodies, compared to antibodies 25D2 and LAY.

DESCRIPTION OF THE INVENTION

Figure 2:
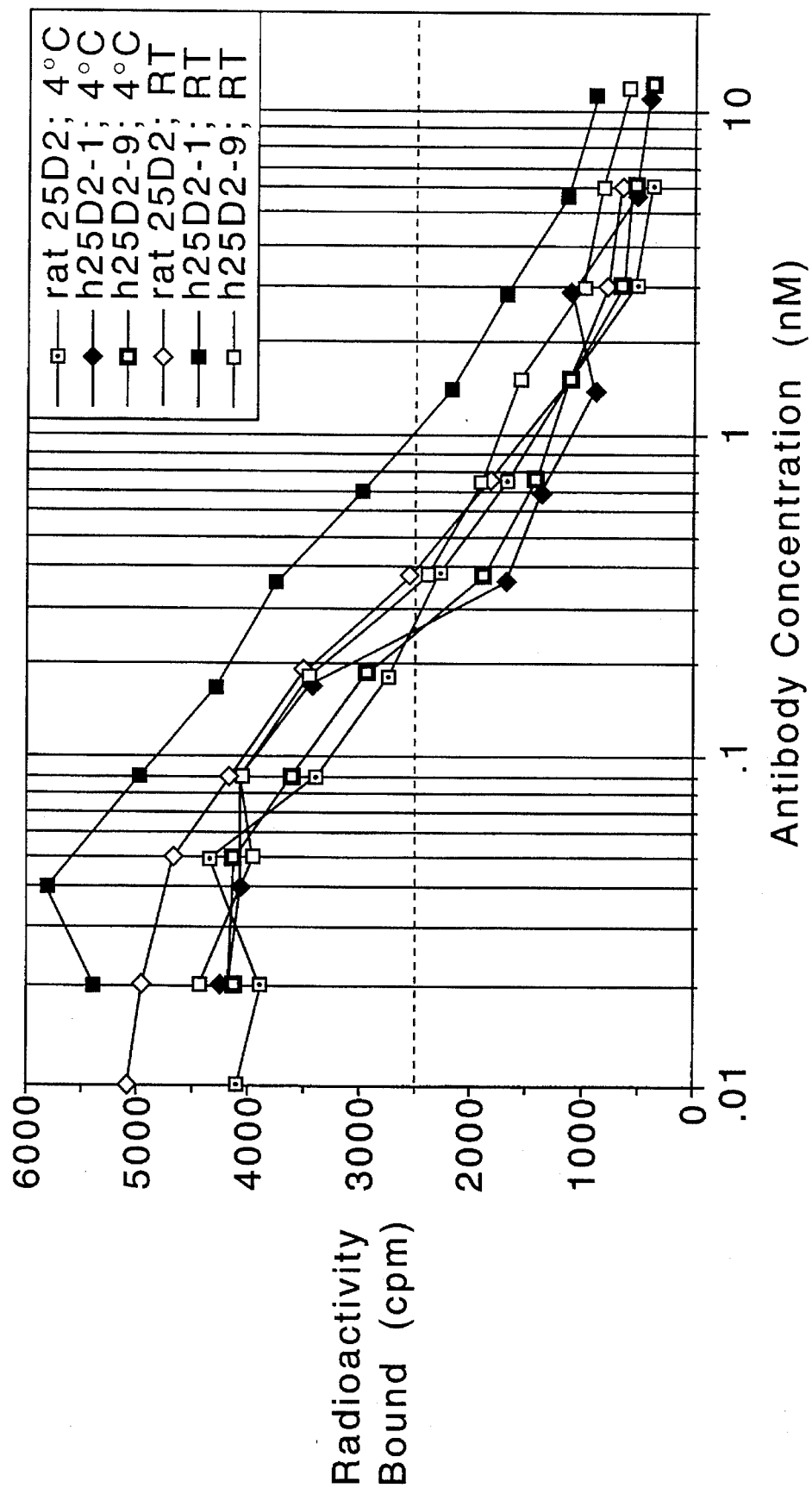
FIG. 2 is a graphical representation of the results of a competition assay in which the effects of varying concentrations of the indicated antibodies on the binding of a fixed amount of human $^{125}$I-IL-4 to immobilized rat antibody 25D2 were measured. Bound radioactivity is shown as a function of free antibody concentration, both at 4° C. and at room temperature.

All references cited herein are hereby incorporated in their entirety by reference.

Much of the work leading to precursor constructs used to make the present invention is described in International Patent Application Publication No. WO 93/17106. Reference should be made to this publication if it is desired to understand the stratey involved in making the humanized antibodies disclosed therein. All of the essential engineering steps required to make the starting constructs used in this invention, however, are detailed below.

As used herein, the terms "DNA" and "DNAs" are defined as molecules comprising deoxyribonucleotides linked in standard 5' to 3' phosphodiester linkage, including both smaller oligodeoxyribonucleotides and larger deoxyribonucleic acids.

Antibodies comprise an assembly of polypeptide chains linked by disulfide bridges. Two principal polypeptide chains, referred to as the light chain and the heavy chain, make up all major structural classes (isotypes) of antibody. Both heavy chains and light chains are further divided into subregions referred to as variable regions and constant regions.

Heavy chains comprise a single variable region and three or four different constant regions, and light chains comprise a single variable region (different from that of the heavy chain) and a single constant region (different from those of the heavy chain). The variable regions of the heavy chain and light chain are responsible for the antibody's binding specificity.

As used herein, the term "heavy chain variable region" means a polypeptide (1) which is from 110 to 125 amino acids in length, and (2) whose amino acid sequence corresponds to that of a heavy chain of a monoclonal antibody of the invention, starting from the heavy chain's N-terminal amino acid. Likewise, the term "light chain variable region" means a polypeptide (1) which is from 95 to 115 amino acids in length, and (2) whose amino acid sequence corresponds to that of a light chain of a monoclonal antibody of the invention, starting from the light chain's N-terminal amino acid.

The terms Fab, Fc, F(ab)$_2$, and Fv are employed with their standard immunological meanings [Klein, *Immunology* (John Wiley, New York, 1982); Parham, Chapter 14, in Weir, ed. *Immunochemistry*, 4th Ed. (Blackwell Scientific Publishers, Oxford, 1986)].

As used herein the term "monoclonal antibody" refers to a homogeneous population of immunoglobulins which specifically bind to an epitope (i.e., antigenic determinant) of human IL-4, the humanized antibody of this invention, or to antigenic fragments thereof.

Antigenic (i.e., immunogenic) fragments of the humanized antibody of this invention may or may not have IL-4-binding capability. Regardless of whether they bind IL-4, such fragments are useful as antigens for preparing antibodies by standard methods. These antibodies, whether polyclonal or monoclonal, can be used, e.g., in an immobilized form bound to a solid support by well known methods, to purify the humanized antibodies by immunoaffinity chromatography.

Antibodies against the antigenic fragments can also be used, unlabeled or labeled by standard methods, as the basis for immunoassays of the humanized antibodies. The particular label used will depend upon the type of immunoassay used. Examples of labels that can be used include but are not limited to radiolabels such as $^{32}$P, $^{125}$I, $^{3}$H and $^{14}$C; fluorescent labels such as fluorescein and its derivatives, rhodamine and its derivatives, dansyl and umbelliferone; chemiluminescers such as luciferia and 2,3-dihydrophthalazinediones; and enzymes such as horseradish peroxidase, alkaline phosphatase, lysozyme and glucose-6-phosphate dehydrogenase.

The antibodies can be tagged with such labels by known methods. For example, coupling agents such as aldehydes, carbodiimides, dimaleimide, imidates, succinimides, bisdiazotized benzadine and the like may be used to tag the antibodies with fluorescent, chemiluminescent or enzyme labels.

The general methods involved are well known in the art and are described, e.g., in *Immunoassay: A Practical Guide*, 1987, Chan (Ed.), Academic Press, Inc., Orlando, Fla. Such immunoassays could be carried out, e.g., on fractions during purification of the humanized antibodies, or on serum samples from patients receiving the humanized antibodies or fragments therefrom having IL-4-binding activity.

Of course, the humanized antibodies themselves or IL-4-binding fragments therefrom can also be used for the immunoaffinity purification or immunoassay of human IL-4.

It is well known in the art that epitopes generally contain at least about five amino acid residues [Ohno et al., Proc. Natl. Acad. Sci. USA 82:2945 (1985)]. Therefore, the antigenic fragments of this invention will typically comprise at least five amino acid residues of the sequence of the complete heavy or light chain of the humanized antibody. Preferably, they will contain at least 7, and most preferably about 10 amino acid residues to ensure that they will be antigenic. Whether a given fragment is immunogenic can readily be determined by routine experimentation.

Such antigenic fragments can be produced by proteolytic cleavage of the antibody or by chemical synthesis or recombinant technology and are thus not limited by proteolytic cleavage sites.

Preferably, smaller antigenic fragments will first be rendered more immunogenic by cross-linking or by coupling to an immunogenic carrier molecule (i.e., a macromolecule having the property of independently eliciting an immunological response in a host animal, to which the polypeptides of the invention can be covalently linked). Cross-linking or conjugation to a carrier molecule may be required because small polypeptide fragments sometimes act as haptens (molecules which are capable of specifically binding to an antibody but incapable of eliciting antibody production, i.e., they are not immunogenic). Conjugation of such fragments to an immunogenic carrier molecule renders them immunogenic through what is commonly known as the "carrier effect".

Suitable carrier molecules include, e.g., proteins and natural or synthetic polymeric compounds such as polypeptides, polysaccharides, lipopolysaccharides etc. Protein carrier molecules are especially preferred, including but not limited to keyhole limpet hemocyanin and mammalian serum proteins such as human or bovine gammaglobulin, human, bovine or rabbit serum albumin, or methylated or other derivatives of such proteins. Other protein carriers will be apparent to those skilled in the art. Preferably, but not necessarily, the protein carrier will be foreign to the host animal in which antibodies against the fragments are to be elicited.

Covalent coupling to the carrier molecule can be achieved using methods well known in the art, the exact choice of which will be dictated by the nature of the carrier molecule used. When the immunogenic carrier molecule is a protein, the fragments of the invention can be coupled, e.g., using water soluble carbodiimides such as dicyclohexylcarbodiimide or glutaraldehyde.

Coupling agents such as these can also be used to cross-link the fragments to themselves without the use of a separate carrier molecule. Such cross-linking into aggregates can also increase immunogenicity. Immunogenicity can also be increased by the use of known adjuvants, alone or in combination with coupling or aggregation.

Suitable adjuvants for the vaccination of animals include but are not limited to Adjuvant 65 (containing peanut oil, mannide monooleate and aluminum monostearate); Freund's complete or incomplete adjuvant; mineral gels such as aluminum hydroxide, aluminum phosphate and alum; surfactants such as hexadecylamine, octadecylamine, lysolecithin, dimethyldioctadecyl-ammonium bromide, N,N-dioctadecyl-N',N'-bis(2-hydroxymethyl) propanediamine, methoxyhexadecylglycerol and pluronic polyols; polyanions such as pyran, dextran sulfate, poly IC, polyacrylic acid and carbopol; peptides such as muramyl dipeptide, dimethylglycine and tuftsin; and oil emulsions. The polypeptides could also be administered following incorporation into liposomes or other microcarriers.

Information concerning adjuvants and various aspects of immunoassays are disclosed, e.g., in the series by P. Tijssen, *Practice and Theory of Enzyme Immunoassays*, 3rd Edition, 1987, Elsevier, N.Y.

Serum produced from animals thus immunized can be used directly. Alternatively, the IgG fraction can be separated from the serum using standard methods such as plasmaphoresis or adsorption chromatography using IgG specific adsorbents such as immobilized Protein A.

As used herein the term "binding composition" means a composition comprising two polypeptide chains (1) which, when operationally associated, assume a conformation having high binding affinity for human IL-4, and (2) which are derived from a hybridoma producing monoclonal antibodies specific for human IL-4.

The term "operationally associated" is meant to indicate that the two polypeptide chains can be positioned relative to one another for binding by a variety of means, including association in a native antibody fragment, such as in an Fab or Fv fragment, or by way of genetically engineered cysteine-containing or other linkers at the carboxyl termini.

Methods for making recombinant Fv fragments based on known antibody heavy and light chain variable region sequences are known in the art, having been described, e.g., by Moore et al. (U.S. Pat. No. 4,642,334) and by Pl˜uckthun [*Bio/Technology* 9:545 (1991)]. Alternatively, they can be chemically synthesized by standard methods.

Hybridomas of the invention used to make monoclonal antibodies against the humanized antibody of the invention or antigenic fragments thereof are produced by well-known techniques. Usually, the process involves the fusion of an immortalizing cell line with a B-lymphocyte that produces the desired antibody. Alternatively, non-fusion techniques for generating immortal antibody-producing cell lines are possible, and come within the purview of the present invention, e.g., virally-induced transformation [Casali et al., Science 234:476 (1986)]. Immortalizing cell lines are usually transformed mammalian cells, particularly myeloma cells of rodent, bovine, and human origin. Most frequently, rat or mouse myeloma cell lines are employed as a matter of convenience and availability.

Techniques for obtaining the appropriate lymphocytes from mammals injected with the target antigen are well known. Generally, peripheral blood lymphocytes (PBLs) are used if cells of human origin are desired, or spleen cells or lymph node cells are used if non-human mammalian sources are desired. A host animal is injected with repeated dosages of the purified antigen, and the animal is permitted to generate the desired antibody-producing cells before these are harvested for fusion with the immortalizing cell line. Techniques for fusion are also well known in the art, and in general involve mixing the cells with a fusing agent, such as polyethylene glycol.

Hybridomas are selected by standard procedures, such as HAT (hypoxanthine-aminopterin-thymidine) selection. From among these hybridomas, those secreting the desired antibody are selected by assaying their culture medium by standard immunoassays, such as Western blotting, ELISA (enzyme-linked immunosorbent assay), RIA (radioimmunoassay), or the like. Antibodies are recovered from the medium using standard protein purification techniques [Tijssen, *Practice and Theory of Enzyme Immunoassays* (Elsevier, Amsterdam, 1985)]. Many references are available for guidance in applying any of the above techniques [Kohler et al., *Hybridoma Techniques* (Cold Spring Harbor Laboratory, New York, 1980); Tijssen, *Practice and Theory of Enzyme Immunoassays* (Elsevier, Amsterdam, 1985); Campbell, *Monoclonal Antibody Technology* (Elsevier, Amsterdam, 1984); Hurrell, *Monoclonal Hybridoma Antibodies: Techniques and Applications* (CRC Press, Boca Raton, Fla., 1982)]. Monoclonal antibodies can also be produced using well known phage library systems.

The use and generation of antibody fragments is also well known, e.g., Fab fragments [Tijssen, *Practice and Theory of Enzyme Immunoassays* (Elsevier, Amsterdam, 1985)], Fv fragments [Hochman et al., Biochemistry 12:1130 (1973); Sharon et al., Biochemistry 15:1591 (1976); Ehrlich et al., U.S. Pat. No. 4,355,023] and antibody half molecules (Auditore-Hargreaves, U.S. Pat. No. 4,470,925).

Hybridomas and monoclonal antibodies of the invention are produced using either glycosylated or unglycosylated versions of the recombinantly-produced humanized antibodies. Generally, unglycosylated versions are produced in *E. coli*, and glycosylated versions are produced in yeast or mammalian cell hosts, e.g., Chinese hamster ovary (CHO), COS monkey or mouse L cells.

The recombinantly-produced humanized antibodies are produced by introducing an expression vector into a host cell using standard protocols [Maniatis et al., *Molecular Cloning: A Laboratory Manual* (Cold Spring Harbor Laboratory, New York, 1982); Okayama and Berg, Mol. Cell. Biol. 2:161 (1982); Okayama and Berg, Mol. Cell. Biol. 3:280 (1983); Hamer, Genetic Engineering 2:83 (1980); U.S. Pat. No. 4,599,308; Kaufman et al., Mol. Cell. Biol. 2:1304 (1982)].

Construction of bacterial or mammalian expression vectors is well known in the art, once the nucleotide sequence encoding a desired protein is known or otherwise available. For example, DeBoer (U.S. Pat. No. 4,511,433) has disclosed promoters for use in bacterial expression vectors. Goeddel et al. (U.S. Pat. No. 4,601,980) and Riggs (U.S. Pat. No. 4,431,739) have disclosed the production of mammalian proteins by *E. coli* expression systems. Riggs (supra), Ferretti et al. [Proc. Natl. Acad. Sci. 83:599 (1986)], Sproat et al. [Nucleic Acids Res. 13:2959 (1985)] and Mullenbach et al. [J. Biol. Chem. 261:719 (1986)] disclose how to construct synthetic genes for expression in bacteria.

The present invention is based upon the surprising discovery that a humanized antibody against human IL-4 disclosed in International Patent Application Publication No. WO 93/17106 could be further engineered using methods not disclosed in the publication to produce a new humanized antibody having markedly superior properties. This new antibody, designated h25D2-9, is characterized in part by activities in an IL-4 competition binding assay and in a bioassay that are comparable to those of rodent monoclonal antibody 25D2, upon which the humanized antibody is based.

Although the best humanized antibody disclosed in International Patent Application Publication No. WO 93/17106, designated h25D2-1, produced similar results in the competition binding assay at 4° C., antibody h25D2-9 appeared to be considerably more potent than antibody h25D2-1 at room temperature. The improved activity shown by antibody h25D2-9 at the higher temperature makes that antibody more suitable for therapeutic use.

New humanized antibody h25D2-9 is further characterized by a surprisingly increased expression in COS cells, compared to the previously disclosed humanized antibodies. Available data suggest that this increased expression, which is five to ten times greater than the expression of antibody h25D2-1 in the same cells, may be due to enhanced chain association within the cells. The present invention, however, is in no way dependent upon whether this possible explanation is correct or not.

Humanized antibody h25D2-9 was designed by introducing further framework modifications into antibody h25D2-1. This procedure, which involved replacement of some non-consensus framework residues with either rodent or consensus human residues, was carried out by following to some extent the rules disclosed by Adair et al. in International Patent Application Publication No. WO 91/09967.

As noted in the Examples below, however, the methods of Adair et al. were followed with modification. Furthermore, there is evidence to show that if the procedures of Adair et al. were applied de novo to rodent monoclonal antibody 25D2, a humanized antibody having the superior characteristics of antibody h25D2-9 could not have been produced. What is required is modification of starting construct h25D2-1 following the rules of Adair et al. as modified herein.

The nucleotide sequences of cDNAs encoding the heavy ($V_H$) and light ($V_L$) chain variable regions of anti-human IL-4 monoclonal antibody 25D2, the production of which is described below, are defined in the Sequence Listing by SEQ ID NOs: 1 and 2, respectively. The amino acid sequences predicted from these nucleotide sequences are also defined in SEQ ID NOs: 1 and 2.

The nucleotide and predicted amino acid sequences of the variable regions of the light and heavy chains of antibody h25D2-9 are shown in SEQ ID NOs: 70 and 79, respectively, although those skilled in the art will appreciate that these sequences also contain subsequences that are not in the variable region. For example, the sequences contain secretory leader sequences that typically are cleaved during post-translational processing in eukaryotic cells. The regions of the sequences which confer IL-4 binding specificity and affinity will be apparent to those skilled in the art, from the disclosure herein.

The variable regions shown in SEQ ID NOs: 70 and 79 can also form the basis for the design of non-peptide mimetic compounds which mimic the functional properties of antibody h25D2-9. Methods for producing such mimetic compounds have been described, e.g., by Saragovi et al. [Science 253:792 (1991)].

In addition to providing a basis for making a superior humanized antibody against human IL-4, the information in SEQ ID NOs: 70 and 79 can be used to produce single-chain IL-4 binding proteins comprising linked heavy and light chain fragments of the Fv region, as described by Bird et al. [Science 242:423 (1988)], or biosynthetic antibody binding sites (BABS), as described by Huston et al. [Proc. Natl. Acad. Sci. USA 85:5879 (1988)]. Single-domain antibodies comprising isolated heavy-chain variable domains [Ward et al., Nature 341:544 (1989)]can also be prepared using the disclosed sequence information.

The present invention can also be used to construct bi-specific antibodies which have binding specificity for another antigen, as well as for IL-4. Such antibodies can be constructed by known methods, e.g., by chemical reassociation of half molecules as described by Brennan et al. [Science 229:81 (1985)].

The variable regions of antibody h25D2-9 can also be coupled together in a polypeptide, either directly or by a linker sequence. One or more of the variable regions can also be engineered into another (non-immunoglobulin) polypeptide or protein, thereby conferring IL-4 binding capability on the polypeptide or protein.

The light and heavy chains of antibody h25D2-9 can also be used in conjunction with the complementary chain from another monoclonal antibody, resulting in a kind of "hybrid" antibody. For example, the heavy chain of antibody h25D2-9 has been combined with the light chain of antibody h25D2-1, and vice versa. If the complementary chain selected is from a rodent antibody specific for human IL-4, such as antibody 25D2, a "semi-humanized" antibody would result. Whether such antibodies have adequate affinity for IL-4 can readily be determined by routine experimentation, using the methods described herein.

Polypeptides "comprising light or heavy chain variable regions of a humanized monoclonal antibody against human IL-4 which have amino acid sequences shown in SEQ ID NO: 70 and SEQ ID NO: 79, respectively, or subsequences of such sequences", are defined herein to include all of the foregoing derivative forms of the specific binding region of antibody h25D2-9.

DNAs which encode the heavy and light chain variable regions of antibody h25D2-9 can be prepared by standard methods using the nucleic acid sequence information provided in SEQ ID NOs: 70 and 79. For example, such DNA can be chemically synthesized using, e.g., the phosphoramidite solid support method of Matteucci et al. [J. Am. Chem. Soc. 103:3185 (1981)], the method of Yoo et al. [J. Biol. Chem. 764:17078 (1989)], or other well known methods. This can be done by sequentially linking a series of oligonucleotide casettes comprising pairs of synthetic oligonucleotides, as described below.

Of course, due to the degeneracy of the genetic code, many different nucleotide sequences can encode polypeptides having the amino acid sequences defined by SEQ ID NOs: 70 and 79 or subsequences thereof. The codons can be selected for optimal expression in prokaryotic or eukaryotic systems. Such degenerate variants are also encompassed by this invention.

Insertion of the DNAs encoding the heavy and light chain variable regions of antibody h25D2-9 into a vector is easily accomplished when the termini of both the DNAs and the vector comprise compatible restriction sites. If this cannot be done, it may be necessary to modify the termini of the DNAs and/or vector by digesting back single-stranded DNA overhangs generated by restriction endonuclease cleavage to produce blunt ends, or to achieve the same result by filling in the single-stranded termini with an appropriate DNA polymerase.

Alternatively, any site desired may be produced, e.g., by ligating nucleotide sequences (linkers) onto the termini. Such linkers may comprise specific oligonucleotide sequences that define desired restriction sites. Restriction sites can also be generated by the use of the polymerase chain reaction (PCR). See, e.g., Saiki et al., Science 239:487 (1988). The cleaved vector and the DNA fragments may also be modified if required by homopolymeric tailing.

Pharmaceutical compositions can be prepared using the monoclonal antibodies, binding compositions, fusion proteins or single-chain binding proteins of the invention, or anti-idiotypic antibodies prepared against such monoclonal antibodies, to treat IL-4-related diseases.

Some of the compositions have IL-4 blocking or antagonistic effects and can be used to suppress IL-4 activity. Such compositions comprise, e.g., the monoclonal antibodies, binding compositions or single-chain binding proteins of the invention and a physiologically acceptable carrier.

Other compositions comprise anti-idiotypic antibodies prepared using the monoclonal antibodies of the invention as an antigen and a physiologically acceptable carrier. These anti-idiotypic antibodies, which can be either monoclonal or polyclonal and are made by standard methods, may mimic the binding activity of IL-4 itself. If they do, they may potentially be useful as IL-4 agonists.

The humanized antibodies of this invention maybe used in the form of complexes in which the antibodies are bound to IL-4. Such complexes may extend the serum half-life of IL-4, and thus produce sustained release, by decreasing the rate of clearance. They may also produce controlled release of the IL-4, as the IL-4 slowly dissociates from the complexes.

Useful pharmaceutical carriers can be any compatible, non-toxic substance suitable for delivering the compositions of the invention to a patient. Sterile water, alcohol, fats, waxes, and inert solids may be included in a carrier. Pharmaceutically acceptable adjuvants (buffering agents, dispersing agents) may also be incorporated into the pharmaceutical composition. Generally, compositions useful for parenteral administration of such drugs are well known; e.g. *Remington's Pharmaceutical Science*, 17th Ed. (Mack Publishing Company, Easton, Pa., 1990). Alternatively, compositions of the invention may be introduced into a patient's body by implantable drug delivery systems [Urquhart et al., Ann. Rev. Pharmacol. Toxicol. 24:199 (1984)].

Therapeutic formulations may be administered in any conventional dosage formulation. Formulations typically comprise at least one active ingredient, together with one or more acceptable carriers. Formulations may include those suitable for oral, rectal, nasal, or parenteral (including subcutaneous, intramuscular, intravenous and intradermal) administration.

The formulations may conveniently be presented in unit dosage form and may be prepared by any methods well known in the art of pharmacy. See, e.g., Gilman et al. (eds.) (1990), *The Pharmacological Bases of Therapeutics*, 8th Ed., Pergamon Press; and *Remington's Pharmaceutical Sciences*, supra, Easton, Penn.; Avis et al. (eds.) (1993) *Pharmaceutical Dosage Forms: Parenteral Medications* Dekker, N.Y.; Lieberman et al. (eds.) (1990) *Pharmaceutical Dosage Forms: Tablets* Dekker, N.Y.; and Lieberman et al. (eds.) (1990), *Pharmaceutical Dosage Forms: Disperse Systems* Dekker, N.Y.

EXAMPLES

The following non-limiting Examples will serve to illustrate the present invention. Selection of vectors and hosts as well as the concentration of reagents, temperatures, and the values of other variables are only to exemplify application of the present invention and are not to be considered limitations thereof.

Unless otherwise indicated, percentages given below for solids in solid mixtures, liquids in liquids, and solids in liquids are on a wt/wt, vol/vol and wt/vol basis, respectively. Sterile conditions were maintained during cell culture.

Example I.

Cloning of Antibody 25D2

General Methods and Reagents

Unless otherwise noted, standard recombinant DNA methods were carried out essentially as described by Maniatis et al., *Molecular Cloning: A Laboratory Manual*, 1982, Cold Spring Harbor Laboratory.

Small scale isolation of plasmid DNA from saturated overnight cultures was carried out according to the procedure of Birnboim et al. [Nuc. Acids Res. 7:1513 (1979)]. This procedure allows the isolation of a small quantity of DNA from a bacterial culture for analytical purposes. Unless otherwise indicated, larger quantities of plasmid DNA were prepared as described by Clewell et al. [J. Bacteriol. 110:1135 (1972)].

Specific restriction enzyme fragments derived by the cleavage of plasmid DNA were isolated by preparative electrophoresis in agarose. Gels measuring 9×5 ½ cm were run at 50 mA for 1 hour in Tris-Borate buffer (Maniatis et al., supra, p. 454) and then stained with 0.5 μg/ml ethidium bromide to visualize the DNA. Appropriate gel sections were excised, and the DNA was electroeluted (Maniatis et al., supra, p. 164). After electroelution, the DNA was phenol extracted (Maniatis et al., supra, p. 458) and ethanol precipitated (Maniatis et al., supra, p. 461).

Restriction enzymes and T4 DNA ligase were purchased from New England Biolabs (Beverly, Mass.). Superscript RNAse H- reverse transcriptase was from BRL/Gibco (Rockville, Md.), Taq DNA polymerase from Stratagene (LaJolla, Calif.), DNA polymerase Klenow fragment from Pharmacia LKB Biotechnology, Inc. (Piscataway, N.J.), calf intestinal phosphatase from Boehringer Mannheim Biochemicals (Indianapolis, Ind.) and RNAsin from Promega (Madison, Wis.). All enzymes were used in accordance with the manufacturers' instructions. The Sequenase version 2.0 sequencing system was obtained from United States Biochemical (Cleveland, Ohio).

Deoxynucleotide triphosphates and oligo $dT_{12-18}$ primer were from Pharmacia LKB Biotechnology, bovine serum albumin from Boehringer Mannheim Biochemicals and redistilled phenol from BRL/Gibco.

The plasmid vector Bluescript was purchased from Stratagene, while competent *E. coli* strain DH5-alpha (Max Efficiency) was from BRL/Gibco.

Tissue culture media and supplements were from BRL/Gibco, and fetal calf serum was from Hyclone Laboratories, Inc. (Logan, Utah).

Cell Culture

Hybridoma cell line MP4.25D2.11 was maintained in RPMI 1640 medium supplemented with 10% heat-inactivated fetal calf serum, 2 mM glutamine and 10 units/ml penicillin/streptomycin in a humidified 37° C. chamber with 5% $CO_2$.

Isolation and Sequencing of Monoclonal Antibody 25D2

Medium conditioned by hybridoma cell line MP4.25D2.11 was concentrated 10–40 fold by ultrafiltration and then applied to a GAMMABIND G®-Agarose column in 0.01 M sodium phosphate, pH 7.0, 0.15M NaCl, with 0.005% sodium azide. GammaBind G-Agarose is a beaded agarose to which recombinant streptococcal Protein G has been covalently immobilized. The bound protein was then eluted with 0.5M acetic acid adjusted to pH 3.0 with ammonium hydroxide. Fractions containing purified monoclonal antibody 25D2 were identified by sodium dodecylsulfate polyacrylamide gel electrophoresis (SDS-PAGE), essentially as described by Laemmli [Nature 227:680 (1970)].

Two methods were used to separate the heavy and light chains of purified antibody 25D2 for sequence determination. The first method employed semi-preparative SDS-PAGE followed by electroblotting onto a polyvinyldifluoride (PVDF) membrane. Briefly, 120 μg (800 pmoles) of the highly purified antibody were subjected to slab gel electrophoresis in SDS after reduction with 2-mercapto-ethanol (Laemmli, supra). The resolved heavy and light chains were then transferred onto an IMMOBILON® membrane (a PVDF membrane from Millipore, Bedford, Mass.), essentially using the electroblotting method of Matsudaira [J. Biol. Chem. 261:10035 (1987)]. The bands corresponding to the heavy and light chains were excised from the membrane following staining with Coomassie Brilliant Blue and processed for N-terminal sequencing.

The other method permitted larger amounts of the heavy and light chains to be isolated in solution. Using this method, a 6 ml sample of purified antibody 25D2 containing 1 mg/ml protein was dialyzed against 0.1M Tris-HCl, 1 mM EDTA, pH 8.0, at 4° C. and then subjected to oxidative sulfitolysis in $NaSO_3/Na_2S_2O_6$, essentially as described by Morehead et al. [Biochemistry 23:2500 (1984)].

Following sulfitolysis, the antibody preparation was dialyzed against 1M acetic acid, lyophilized to dryness, reconstituted in 1M acetic acid to a volume of 1.5 ml, and subjected to gel filtration in a 1×30 cm SEPHADEX G-75® column (Pharmacia, Piscataway, N.J.) equilibrated with the same buffer.

Fractions enriched in heavy and light chains were pooled separately and separately subjected to gel filtration in a 1.5×100 cm SEPHADEX G-75® column in 1M acetic acid. The purity of the heavy and light chains following this step was assessed by analytical SDS-PAGE. Fractions containing the heavy (4 nmoles) and light (3 nmoles) chains were pooled separately and concentrated in vacuo to about 0.1 ml-volumes for sequencing.

All N-terminal amino acid sequencing was performed using an Applied Biosystems Model 477A protein-peptide sequencer. Sequencing of the isolated heavy and light chains blotted onto the IMMOBILON® membrane was carried out essentially as described by Yuen et al. [Biotechniques 7:74 (1989)]. Analysis of the isolated chains in solution was performed following the instructions of the manufacturer of the sequencer.

Oligonucleotide Primer Design and Cloning Strategy

Based upon information obtained from the foregoing amino acid sequence analyses, degenerate oligonucleotide primers were designed for use in PCR. One degenerate primer designated B1798 had a nucleotide sequence encoding the amino-terminal 13 amino acid residues of the mature heavy chain of 25D2. Another degenerate primer designated B1873 had a nucleotide sequence encoding the amino-terminal 7 amino acid residues of the mature light chain of the antibody.

A non-degenerate oligonucleotide primer designated B1797 having a nucleotide sequence corresponding to a segment in the 3' untranslated region of DNA encoding the antibody heavy chain [Bruggemann et al., Proc. Natl. Acad. Sci. USA 83:6075 (1986)] was also designed, as was a non-degenerate oligonucleotide primer designated B1868 having a nucleotide sequence corresponding to a segment in the kappa constant region of DNA encoding the antibody light chain [Sheppard et al., Proc. Natl. Acad. Sci. USA 78:7064 (1981)].

Other non-degenerate primers were designed for use in isolation of cDNA encoding the variable regions of the heavy and light chains of antibody 25D2, based upon nucleotide sequence information obtained following PCR amplification of cDNA encoding the complete heavy and light chains.

Oligonucleotide Synthesis

Oligonucleotide primers having sequences defined in the Sequence Listing were synthesized by standard methods using an Applied Biosystems Model 380B Synthesizer.

The designations of these primers, followed in parentheses by the corresponding sequence identification numbers, are as follows:

B1797 (SEQ ID NO: 5)
B1798 (SEQ ID NO: 6)
B1868 (SEQ ID NO: 7)
B1873 (SEQ ID NO: 8)
B1884 (SEQ ID NO: 9)
B1902 (SEQ ID NO: 10)
B1921 (SEQ ID NO: 11)
B1922 (SEQ ID NO: 12)
B1932 (SEQ ID NO: 13)
T3 (SEQ ID NO: 14)
T7 (SEQ ID NO: 15)

Primers B1798 and B1873 were designed to define a 5' NotI restriction site to facilitate cloning. Primers B1797 and B1868 were designed to define a 3' SpeI restriction site, for the same reason.

RNA Isolation

Total cytoplasmic RNA was isolated from hybridoma cell line MP4.25D2.11 by incubating the cells for 15 minutes in a lysis buffer consisting of 10 mM Tris-HCl, pH 7.4, 10 mM NaCl, 2 mM $MgCl_2$ and 0.5% Nonidet P40 (an octylphenol-ethylene oxide condensate containing an average of 9 moles ethylene oxide per mole of phenol). After a centrifugation step at 2,000× g for 5 minutes at 4° C., the nuclear pellet was discarded and the supernatant fluid was re-centrifuged at 10,000× g for 15 minutes at 4° C.

After the second centrifugation step, the supernatant fluid was mixed with an equal volume of a solution containing 200 mM NaCl, 10 mM Tris-HCl, pH 7.4, 20 mM ethylenediaminetetraacetate (EDTA) and 2% sodium dodecylsulfate (SDS). The mixture was extracted once with an equal volume of Tris-buffered phenol/chloroform (1:1) and once with chloroform. Following the extractions, the mixture was precipitated overnight with 1/20 volume of 0.2M sodium acetate, pH 5.5, and 2.5 volumes of absolute ethanol at −20° C.

First Strand Synthesis

First strand cDNA was synthesized directly from total cytoplasmic RNA at 37° C. for 90 minutes in a 10 μl reaction volume. The reaction mixture contained 5.6 μl of RNA in diethylpyrocarbonate-treated distilled $H_2O$, 0.25 μl of RNAsin (40,000 units/ml), 2 μl of 5X reverse transcriptase reaction buffer (250 mM Tris-HCl, pH 8.3, 200 mM KCl, 30 mM $MgCl_2$, 3 mM dithiothreitol), 0.25 μl of bovine serum albumin (4 mg/ml), 1 μl of 10 mM dNTP mixture (dATP, TTP, dCTP, dGTP), 0.4 μl of oligo dT primer (0.5 mg/ml) and 0.5 μl of Superscript RNase H- reverse transcriptase (200 units/ml).

Polymerase Chain Reaction

PCR amplifications were carried out using a Techne programable thermal cycler. The PCR reaction mixtures consisted of 10 μl of first strand cDNA reaction mixture, 53.5 ml of distilled $H_2O$, 10 μl of 10X Taq polymerase reaction buffer (500 mM KCL, 100 mM Tris-HCl, pH 8.3, 15 mM $MgCl_2$, 0.1% gelatin), 16 μl of 1.25 mM dNTP mixture (dATP, TTP, dCTP, dGTP), 5 μl of each primer of interest (20 pmol/μl) and 0.5 μl of *Thermus aquaticus* DNA polymerase.

The PCR conditions included 30 cycles of: denaturation at 95° C. for 2 minutes, primer annealing at 37° C. for 2 minutes, primer extension at 72° C. for 3 minutes and a final extension period of 9 minutes at 72° C. At the end of amplification, 1 μl of 100 mM dNTP mixture and 1 μl of DNA polymerase Klenow fragment (5 units/μl) were added to each of the PCR reactions, and the fill-in step was allowed to proceed for 10 minutes at room temperature.

The PCR mixtures were subjected to electrophoresis in 1% agarose/Tris-borate gels containing 0.5 μg/ml ethidium bromide. The PCR fragments of interest were excised from the gels and purified by electroelution.

Subcloning and DNA Sequencing

The gel-purified PCR fragments were digested with NotI and SpeI and then ligated to dephosphorylated NotI/SpeI-digested Bluescript plasmid vector at 15° C. for 16–24 hours in a mixture containing 50 mM Tris-HCl, pH 7.5, 10 mM $MgCl_2$, 10 mM dithiothreitol, 50 μg/ml bovine serum albumin, 1 mM ATP and 10 units of T4 DNA ligase. Competent *E. coli* strain DH5-alpha (Max Efficiency) cells were transformed with the ligation mixture.

Diagnostic analysis of the resulting transformants was carried out by restriction digests with NotI and SpeI, as well as by PCR with the oligonucleotide primers used in the initial PCR reactions. The inserts of the subclones of interest were subjected to DNA sequencing using the Sequenase system.

Oligonucleotide primers T7, B1884, B1921 and B 1922 were used to obtain DNA encoding the variable region of the heavy chain. Primers T3, B1902 and B1932 were used to obtain DNA encoding the variable region of the light chain.

CDR Determinations

The CDRs within the variable regions of the heavy and light chains of monoclonal antibody 25D2 were determined both by the method of Kabat et al., [*Sequences of Proteins of Immunological Interest*, 4th Edition, 1987, U.S. Department of Health and Human Services, National Institutes of Health], and by computer binding site loop analysis. For the latter analysis, a Silicon Graphics Personal Iris Model 4D/25 computer was employed using Sybyl or IMPACT software. The approach taken involved essentially a combination of the three-dimensional modeling methods of Seville et al. [Biochemistry 27:8344 (1988)], the immunoglobulin hypervariable region conformation analytical methods of Chothia et al. [J. Mol. Biol. 196:901 (1987); Nature 342:877 (1989)] and the protein loop conformation analytical methods of Tramontano et al. [PROTEINS: Structure, Function and Genetics 6:382 (1989)].

Example II

Antibody Humanization

General Methods and Reagents

Restriction enzymes and DNA modifying enzymes were from New England Biolabs. Taq polymerase was obtained from Perkin-Elmer Cetus, Inc. Mouse anti-human IgG4-Fc antibody was purchased from CalBiochem. Sheep anti-human IgG (H+L) peroxidase conjugate and human IgG4 protein standards were obtained from The Binding Site, Inc. Goat anti-rat IgG was purchased from Jackson Immuno-Research Labs.

Purified human IL4 (hIL4) was obtained from a bacterial expression system essentially as described by Lundell et al. [J. Indust. Microbiol. 5:215 (1990)] and radioiodinated by the IODOGEN® (Pierce Chemical Co.) method, according to the manufacturers instructions. A purified rat monoclonal antibody, designated 25D2, has been described by DeKruyff et al. [J. Exp. Med. 170:1477 (1989)].

Human growth hormone (hGH) standards and a goat anti-rabbit IgG peroxidase conjugate were purchased from Boehringer-Mannheim Biochemicals, Inc. Rabbit anti-hGH was from Dako Corp., and sheep anti-hGH was obtained from Biodesign International. Protein-G SEPHAROSE® CL-4B was purchased from Pharmacia, Inc. Oligonucleotides were synthesized using an Applied Biosystems (ABI) 380B DNA synthesizer.

Bacterial Strains, Plasmids, Cell Lines and Recombinant DNA Methods

All plasmids were propagated in *E. coli* K-12 strain MM294 (ATCC 33625). Bluescript (KS) and Bluescribe plasmids were obtained from Stratagene Inc. Plasmids pDSRS (ATCC 68232) and pSRS (ATCC 68234) are available from the American Type Culture Collection (ATCC). Plasmid HuCK encoding the human kappa constant region and plasmid p24BRH encoding the human IgG4 constant region were obtained from the ATCC (under Accession Nos. ATCC 59173 and ATCC 57413, respectively). Plasmid vectors pUC19 and pSV.Sport were from BRL/GIBCO (Gaithersburg, Md.).

COS 7 cells obtained from the ATCC (ATCC CRL 1651) were propagated in Dulbecco's Modified Eagle's Medium (DMEM)/high glucose supplemented with 10% FBS and 6 mM glutamine. CHO cell line DXB11 was obtained from Dr. L. Chasin (Columbia University, NY, N.Y.) and was propagated before transfection in Ham's F12 medium supplemented with 10% FBS, 16 mM glutamine, 0.1 mM nonessential amino acids, 0.1 mM hypoxanthine and 0.016 mM thymidine. Transfected CHO cells were propagated in DMEM/high glucose supplemented with 10% dialyzed FBS, 18 mM glutamine, and 0.1 mM nonessential amino acids for selection.

A Jijoye cell line stably transformed by a recombinant vector comprising a human growth hormone reporter gene operably linked to a human germline e transcript promoter (called C12 cells) and a Jijoye cell line expressing large quantities of the human IL-4 receptor on the cell surface (called CJ cells) were obtained from Dr. Chung-Her Jenh at Schering-Plough Corporation. Both cell lines were propagated in RPMI (Gibco) containing 15% horse serum, 5% FBS, 6 mM glutamine, 0.1 mM nonessential amino acids, 0.5 mg/ml geneticin (Gibco). Unless otherwise stated, recombinant DNA methods were performed as described by Maniatis et al., supra.

PCR was performed under standard conditions [Saiki et al., Science 230:1350 (1985)], and the sequences of fragments generated by PCR were confirmed by either manual or automated DNA sequencing. Manual DNA sequencing was performed with SEQUENASE® (United States Biochemical Co.) according to the manufacturer's instructions. Automated DNA sequencing was performed on an ABI 373A DNA sequencer using the Taq polymerase cycle sequencing kit provided by ABI, according to the manufacturer's recommendations. Plasmid DNA was prepared for transfections using Qiagen columns (Qiagen, Inc.), according to the manufacturer's instructions.

Determination of Antibody Concentrations by Enzyme-linked Immunosorbent Assay (ELISA)

Antibody concentrations were determined by an IgG4-specific ELISA. Briefly, Nunc MAXISORB® Immunoplates were coated at 4° C. for at least 4 hours with a mouse anti-human IgG4-Fc monoclonal antibody at 5 μg/ml in 50 mM bicarbonate buffer, pH 9.5. The plates were blocked for 1 hour at room temperature in Blocking buffer [3% bovine serum albumin (BSA) in Dulbecco's modified phosphate buffered saline (PBS; Gibco-BRL)]. After washing the plates with Wash buffer (10 mM potassium phosphate, pH 7.4, 0.05% Tween-20), serially diluted samples, either as purified antibodies or conditioned medium, in a volume of 100 μl were applied to the wells of the plates.

Conditioned medium containing the humanized antibodies was typically concentrated 10–30-fold by centrifugation filtration (Amicon, Inc) prior to assay. The plates were incubated for 1–2 hours at room temperature, after which the samples were aspirated and the wells were washed 3 times. One hundred microliters of anti-human IgG (H+L) peroxidase conjugate were added to each well and the plates were incubated for 1 hour at room temperature. The plates were then washed 3 times and 100 μl of ABTS peroxidase substrate (Boehringer-Mannheim Biochemicals) was added to each well for detection of the immune complexes. The plates were read spectrophotometrically at 405 nm.

Transfections

For each of the recombinant antibodies described below, 5 μg of both the heavy and light chain plasmids were transfected into 5×10$^6$ COS 7 cells in a total volume of 250 μl by electroporation using a Biorad Gene Pulser. After 4 hours, the medium (DMEM plus 10% FBS) was replaced with DMEM minus serum. The cells were propagated for 72 hours, after which the medium was harvested, clarified by centrifugation, and stored at −20° C. for subsequent antibody purification. To obtain larger quantities of the humanized antibodies, recombinant CHO cell lines were established that produced antibodies designated h25D2-1 or h25D2-4.

To isolate stable CHO cell lines, 20 μg of the appropriate heavy and light chain plasmid DNAs [molar ratio of heavy chain plasmid:light chain plasmid (with the dhfr gene) 10:1] were transfected into 5×10$^6$ CHO DXB11 cells by the calcium phosphate precipitation method [Graham et al., Virology 52:456 (1973)]. After two days, the cells were selected for resistance to hypoxanthine and thymidine starvation, i.e. dhfr expression [Schimke et al., Methods in Enzymology 151:85 (1987)].

Clones secreting antibody were identified by ELISA, expanded and subjected to methotrexate-mediated gene amplification. Clones secreting the greatest amount of antibody were expanded into roller bottles, and the serum-free medium was harvested continuously. Confluent roller bottle cultures were propagated in serum-containing medium for 48 hours, after which the cells were rinsed with Dulbecco's Modified PBS and the medium was replaced with a serum-free preparation. The serum-free medium was harvested after 3–4 days for subsequent antibody purification.

Antibody Purification

Serum-free conditioned medium containing the antibodies was passed over a Mab TRAP® column of streptococcal protein G-SEPHAROSE® CL-4B (Pharmacia), and the antibodies were eluted according to the manufacturer's instructions. Final antibody concentrations were determined by ELISA as described above.

Affinity Measurements

A. Affinity Constants

To determine whether the humanized antibodies were capable of binding human IL-4, apparent dissociation constants were determined by coating immunoplates with mouse anti-human IgG4-Fc (capture antibody) and blocking the plates as described above for the ELISA assay. After washing the wells, the plates were incubated at room temperature for 2 hours with concentrated conditioned medium containing one of the humanized antibodies (100 μl/well). Wild-type rat antibody 25D2 was assayed in parallel for comparison, using an anti-rat IgG as the capture antibody.

The wells were washed and incubated with $^{125}$I-hIL-4 at concentrations between 4,000 and 2 pM in final volumes of 100 μl. All assays were performed in triplicate, and the background binding was determined by using a 1000-fold molar excess of unlabelled hIL4 in control wells. After incubation for 2 hours at room temperature, the wells were washed, the protein was solubilized in 75 μl of Solubilization buffer [0.1N NaOH/1% sodium dodecylsulfate (SDS)], and the solution was counted in an LKB gamma counter. Concentrations of bound and free hIL4 were determined, and the affinities of the antibodies were determined by Scatchard plot analysis [Berzofsky et al., in *Fundamental Immunology*, 1984, Paul, E. E., Ed., Raven Press, New York, N.Y., pp. 595–644].

B. Competitive Binding Analysis

A comparison of antigen binding by wild-type rat antibody 25D2 and the humanized antibodies was made using a plate binding competition assay in which the binding of labelled human IL-4 ($^{125}$I-hIL-4) to plates coated with antibody 25D2 was measured in the presence of unlabelled antibody 25D2, humanized antibody h25D2-1 or humanized antibody h25D2-4, all of which had been purified.

Immunosorb plates were coated with a 60 ng/ml solution of the rat 25D2 antibody diluted in PBS (100 μl/well) for at least 16 hours at 4° C. The wells were then blocked with Blocking buffer (3% BSA in PBS) for 4 hours at room temperature. Fifty microliters of 2-fold serially diluted competing antibodies plus the appropriate amount of $^{125}$I-hIL-4 (60 μl total volume) were added to each well, and the plates were incubated at room temperature for 16–24 hours. The plates were washed 3 times with potassium phosphate, pH 7.4, plus 0.05% Tween 20. The wells were aspirated dry, and 75 μl of Solubilization buffer (0.1N NaOH/1% SDS) was added to each well and incubated for 30 minutes at room temperature. The solution was removed from each well and counted in an LKB gamma counter.

Inhibition of Receptor Binding

The humanized antibodies were assayed for the ability to inhibit the binding of radiolabelled hIL-4 to the recombinant human IL-4 receptor expressed on Jijoye CJ cells in microtiter plates. Briefly, the humanized antibodies were serially diluted in cell growth medium at protein concentrations of from 8.6 nM to 4 pM. Rat antibody 25D2 was similarly diluted and used as a positive control. Jijoye CJ cells (10$^5$ cells) and 44 pM $^{125}$I-hIL-4 were then added to each well (200 μl final volume per well) and the plates were incubated for 2 hours at 4° C.

After the incubation, the contents of the wells were mixed and 185 μl were removed and layered onto sucrose cushions (150 μl of 5% sucrose in growth medium plus 0.02% sodium azide). After centrifugation (1500 rpm, 4° C., 10 minutes), the tubes were quick-frozen in liquid nitrogen, and the bottoms of the tubes containing the cell pellets were clipped and counted in a gamma counter. Bound cpm was plotted vs. the antibody concentration, and the humanized antibodies were compared to the native antibody at the concentrations required to cause 50% inhibition of receptor binding (IC$_{50}$).

Germline Epsilon Promoter Reporter Gene Assay

Jijoye C12 cells were seeded into 96 well dishes at a density of 4×10$^5$ cells/125 μl/well in medium. Serially diluted test antibodies and 1 ng/mL hIL-4 were added to the cells, and the plates were incubated at 37° C. for about 64 hours. After the incubation, 100 μl of the conditioned medium were removed from each well and added to individual wells of an immunoplate previously coated with a 1:2000 dilution of sheep anti-human growth hormone (αhGH) in sodium carbonate buffer, pH 9.5. The plates were incubated at room temperature for 2 hours and washed 5 times with 10 mM potassium phosphate buffer containing 0.05% Tween-20. One hundred microliters of a rabbit anti-human growth hormone antiserum (diluted 1:1000) were added to each well, and incubation was continued for 1 hour.

The wells were washed again as described above, and 100 μl of a horse-radish peroxidase conjugated goat anti-rabbit IgG (diluted 1:10,000) was added to each well. After washing, 100 μl of ABTS peroxidase substrate was added to the wells for detection of the immune complexes. The plates were read spectrophotometrically at 405 nm.

Optical density (O.D.) at 405 nm was plotted vs. antibody concentration, and the humanized antibodies were compared to the native antibody at the concentrations required to cause 50% inhibition of the expression of the human growth hormone under the control of the germline ε promoter ($IC_{50}$).

Humanized Antibodies

Homology Modeling

Using the methods described above, it was determined that antibody LAY was an optimal human. framework candidate. LAY heavy and light chain pairs were first pursued.

A listing of potential minimal and maximal 25D2 residues that could be grafted into the framework sequences were determined by the above-described methods to be as shown in Table 1.

TABLE 1

|  | Residues[a] |
|---|---|
| $V_H$ Minimal List: | 28,30,31,32,53,54,56,100, 101,103,105,106,107 |
| $V_H$ Maximal List[b]: | 33,35,50,51,52,57,58 59,61,65,109,110 |
| $V_L$ Minimal List: | 29,30,31,50,52,91,94 |
| $V_L$ Maximal List[b]: | 24,34,46,49,53,54,56 |

[a]Residues for $V_H$ and $V_L$ refer to the residue numbers in SEQ ID NO: 1 and SEQ ID NO: 2, respectively.
[b]The $V_H$ and $V_L$ Maximal Lists include the corresponding Minimal Lists and the further indicated residues.

Specific constructs described below contain the following residues from the foregoing Table:

TABLE 2

| Humanized Antibody | Residues | |
|---|---|---|
| h25D2H-1, L | $V_H$ LAY Maximal; | $V_L$ LAY Maximal |
| h25D2H-1, L-1 | $V_H$ LAY Maximal; | $V_L$ LAY Maximal (less residues 46 and 49) |
| h25D2H-2, L-1 | $V_H$ LAY Maximal; (less residues 33 and 35) | $V_L$ LAY Maximal (less residues 46 and 49) |
| h25D2H-3, L-1 | $V_H$ LAY Maximal; (less residues 28 and 30) | $V_L$ LAY Maximal (less residues 46 and 49) |
| h25D2H-4, L-1 | $V_H$ LAY Maximal; (less Residues 28, 30 and 65) | $V_L$ LAY Maximal (less residues 46 and 49) |
| h25D2H-5, L-1 | $V_H$ LAY Maximal; (less residues 33, 35 and 65) | $V_L$ LAY Maximal (less residues 46 and 49) |

Construction of Humanized 25D2 Light Chain Expression Vectors

The nucleotide sequence of DNA for an initial version of the humanized 25D2 light chain (h25D2L), including (from 5' to 3') fifteen 5' noncoding bases and bases encoding an initiating methionine residue, a leader sequence and the variable region of the antibody, together with the corresponding amino acid sequence of the leader and the antibody, is defined in the Sequence Listing by SEQ ID NO: 16.

In the construction of this humanized light chain, silent restriction endonuclease cleavage sites were deduced from the Genetics Computer Group (GCG; Madison, Wis.) SILENT MAP® program. Nucleotide sequences selected to encode the protein sequence utilized codons found in the rat 25D2 sequence, although several codons were changed to create restriction endonuclease cleavage sites.

The entire variable region of the antibody was cloned as three contiguous DNA fragments that were synthesized as pairs of oligonucleotides. These pairs of oligonucleotides were amplified by PCR and joined at unique restriction endonuclease cleavage sites. The result was three fragments (numbered from 5' to 3') delineated by EcoRI/KpnI (fragment 1), KpnI/PstI (fragment 2) and PstI/MscI (fragment 3) sites. In the amplification reactions, the two oligonucleotides in each pair were complementary to each other over a stretch of 18–24 nucleotides. Therefore each oligonucleotide served as a template for the other.

The designations of these oligonucleotide primers, followed in parentheses by the corresponding sequence identification numbers, were as follows:

2481 (SEQ ID NO: 17)
2482 (SEQ ID NO: 18)
2700 (SEQ ID NO: 19)
2641 (SEQ ID NO: 20)
2483 (SEQ ID NO: 21)
2491 (SEQ ID NO: 22)
2662 (SEQ ID NO: 23)
2661 (SEQ ID NO: 24)

The synthesis of fragment 1 required two PCR amplifications. An initial PCR using primers 2481 and 2482 generated a fragment lacking a translational initiation sequence and the leader peptide coding sequence. This fragment was reamplified with primers 2700 and 2641 to add on an EcoRI site followed by the translational initiation and leader peptide coding sequences. The final fragment 1 thus contained at it's 5' terminus an EcoRI site followed by a translational initiation sequence [Kozak, Nucleic Acids Res. 12:857 (1984)] and a sequence encoding a leader peptide corresponding to the anti-CAMPATH-1 antibodies [Reichmann et al., Nature 332:323 (1988)].

The fragment 1 sequence extended through a KpnI site and encoded amino acid residues 1-36 of the variable region of the humanized light chain. Fragment 2 encoded residues 36–79 of the humanized light chain, including a KpnI and PstI site at the 5' and 3' termini, respectively. Fragments 1 and 2 were joined at the unique KpnI site and subcloned into the Bluescript (KS) vector between the EcoRI and PstI sites in the vector to create fragment 1-2. Fragment 3 encoded the remaining amino acids of the variable domain (residues 78–106) and extended from the PstI site through an MscI site (located 22 bases upstream of the 3' terminus of the variable domain), and included an EcoRI site at the 3' end.

Fragment 3 was subcloned into a Bluescript (KS) vector between the PstI and EcoRI sites in the vector. A 321 bp fragment (fragment 4) containing 22 nucleotides at the 3' end of the humanized variable region, including the MscI site, joined to the coding sequence for the entire human kappa constant region, was generated by PCR using the HuCK plasmid as template and primers 2856 and 2857, the sequences of which are defined by SEQ ID NO: 25 and SEQ ID NO: 26, respectively. In addition to the MscI site at the 5' end of fragment 4, an EcoRI site was included on the 3' end to facilitate cloning.

Fragment 4 was joined to fragment 3 between the common MscI site within the variable region and the EcoRI site present on the 3' end of fragment 4 and the vector. An EcoRV site was present downstream of fragment 3–4 in the vector. Fragment 3–4 was removed as a PstI/EcoRV fragment and was ligated to fragment 1–2 between the common PstI site in the variable region and the blunt-ended SmaI site in the vector. The entire coding region for the h25D2L light chain could be obtained after cleavage at the SalI and BamHI sites flanking the coding region in the Bluescript vector.

The mammalian expression vector was constructed by first cleaving the Bluescript vector containing the h25D2L sequence at the 3' end with BamHI, and then treating the cleavage product with Klenow fragment DNA polymerase, under conditions that left flush ends. Next, the h25D2L DNA fragment was obtained after cleavage at the 5' end with SalI. Finally, the h25D2L coding region was ligated to vector pDSRS which had previously been digested with SalI and SmaI. The completed vector, designated pSDh25L, contained the entire coding region for the humanized 25D2 antibody including the signal peptide and the human kappa constant region.

Co-transfection of the foregoing h25D2L DNA with a heavy chain DNA (designated h25D2H-1; prepared as described below) into COS 7 cells did not produce measurable antibody expression, although antibody expression was observed when the h25D2L DNA was co-transfected with DNA for a humanized heavy chain from an unrelated antibody (data not shown).

Since the h25D2L light chain was capable of being expressed with an unrelated heavy chain, it was possible that the sequence of either the humanized 25D2 light chain or the humanized heavy chain was inhibiting h25D2 antibody expression.

Examination of the Fv interface of the 25D2 molecular model suggested that replacement of the human LAY residues leucine 46 and tyrosine 49 with animal residues phenylalanine 46 and phenylalanine 49 could affect the ability of h25D2L to combine with the heavy chain. In addition, comparison of human kappa chain variable region sequences in the Swiss-Prot protein database (Bairoch, Amos) and the human kappa light chain subgroup I according to Kabat et al., *Sequences of Proteins of Immunological Interest*, supra, revealed that the leucine at amino acid position 46 and the tyrosine at amino acid position 49 were highly conserved. Therefore, the foregoing humanized light chain gene was reconstructed to introduce mutations at these positions. In addition, an arginine residue at position 107 that had been omitted in the h25D2L DNA was replaced.

To modify the h25D2L DNA, two pairs of oligonucleotide primers were synthesized to perform PCR-based mutagenesis of the h25D2L coding region. Primer 3016 (SEQ ID NO: 28), which was used as the 5' primer, encompassed the coding region for amino acid residues 38–51 of the light chain variable domain and included a StuI site at the 5' end. Primer 3016 also incorporated three nucleotide changes into the h25D2L sequence. This resulted in replacement of a phenylalanine residue with a leucine residue (F46L) at position 46 of the amino acid sequence, and replacement of a phenylalanine residue at position 49 with a tyrosine codon (F49Y) at position 49. A 3' primer designated 3017 (SEQ ID NO: 29) encompassed the PstI site at position 237.

A 126 bp fragment was generated by PCR using oligonucleotide primers 3016 and 3017 and the h25D2L Bluescript plasmid as template DNA. The StuI/PstI PCR fragment was used to replace the corresponding fragment in vector h25D2L, thereby incorporating the F46L, F49Y changes.

An oligonucleotide primer designated 3018 (used as a 5' primer; SEQ ID NO: 30) was synthesized which encompassed amino acid residues 95–106 of the light chain variable region, including the MscI site at the 5' terminus, and the first three residues of the human kappa constant region. In addition, a codon for arginine (R107) was inserted at the junction of the variable and constant regions in the primer. Another primer designated 3019 (SEQ ID NO: 31) was synthesized to serve as a 3' primer. This primer corresponded to sequences in the Bluescript vector including the BamHI and SpeI sites.

Using primers 3018 and 3019 and the h25D2L Bluescript plasmid as template, a fragment was generated by PCR that included residues 95–107 of the variable domain and the entire coding region of the human kappa chain. This MscI/SpeI PCR fragment was used to replace the corresponding fragment in the F46L, F49Y vector described above. After confirming the DNA sequence of the PCR fragments, the vector was digested with SpeI and treated with Klenow fragment DNA polymerase under conditions that generated flush-ended termini. A fragment containing the entire coding region of humanized antibody light chain h25D2L-1 was isolated after SalI digestion and ligated to the pDSRS vector previously digested with SalI and SmaI. The resulting h25D2L-1 expression vector containing the F46L, F49Y, and R107 mutations of h25D2L was designated pKM20.

The nucleotide sequence of the DNA for the modified version of the humanized 25D2 light chain, including (from 5' to 3') fifteen 5' noncoding bases and bases encoding an initiating methionine residue, a leader sequence and the variable region of the antibody, together with the corresponding amino acid sequence of the leader and the antibody, is defined in the Sequence Listing by SEQ ID NO: 27.

Construction of Humanized 25D2 Heavy Chain Expression Vectors

The nucleotide sequence of DNA for an initial version of the humanized 25D2 heavy chain (h25D2H-1), including (from 5' to 3') fifteen 5' noncoding bases and bases encoding an initiating methionone residue, a leader sequence and the variable region of the antibody, together with the corresponding amino acid sequence of the leader and the antibody, is defined in the Sequence Listing by SEQ ID NO: 32. The nucleotide sequences that were selected to encode the protein sequence, including the signal peptide, utilized codons found in the rat 25D2 sequence. Several codons were changed to create restriction endonuclease cleavage sites.

The entire variable region was cloned as three contiguous DNA fragments that were synthesized as pairs of oligonucleotides. These pairs of oligonucleotides were amplified by the PCR and joined at unique restriction endonuclease cleavage sites. The result was three fragments (numbered from 5' to 3') delineated by SalI/SmaI (fragment 1), SmaI/PstI (fragment 2) and PstI/ApaI (fragment 3) sites. In the amplification reactions, the two oligonucleotides in each pair were complementary to each other over a stretch of 18–24 nucleotides. Therefore each oligonucleotide served as a template for the other.

The designations of these oligonucleotide primers and the corresponding SEQ ID NOs defining their sequences were as follows:

| Oligonucleotide | SEQ ID NO. |
| --- | --- |
| 2588 | 33 |
| 2589 | 34 |
| 2232 | 35 |
| 2445 | 36 |
| 2446 | 37 |
| 2447 | 38 |
| 2523 | 39 |
| 2580 | 40 |
| 2642 | 41 |
| 2646 | 42 |

The synthesis of fragment 1 required two amplification reactions. An inital PCR product of primers 2588 and 2599 was subjected to a second round of amplification with oligonucleotides 2232 and 2445, to yield fragment 1. The final fragment 1 thus contained at its 5' terminus a SalI site followed by a translational initiation sequence (Kozak, supra) and a sequence encoding the leader peptide corresponding to the anti-CAMPATH-1 antibodies (Reichmann et al., supra). The fragment 1 sequence extended through a SmaI site and included the coding sequence for amino acid residues 1-42 of the variable region of the humanized heavy chain.

Fragment 2 encoded residues 42–82 of the humanized heavy chain, including a SmaI site and a PstI site at the 5' and 3' ends, respectively. Fragments 1 and 2 were joined at the unique Sinai site and subcloned into the Bluescript (KS) vector between the SalI and PstI sites in the vector, to create plasmid pBS1-2.

Fragment 3 encoded the remaining amino acids of the variable domain (residues 81–121) and extended from the PstI site through the 3' terminus of the variable region and on through thirty nucleotides of the coding sequence for the human IgG4 constant region. A unique ApaI site was located within sixteen nucleotides of the IgG4 constant sequence in fragment 3. The synthesis of fragment 3 also required two amplification reactions. An initial PCR product of primers 2523 and 2580 was subjected to a second round of amplification with primers 2642 and 2646, to yield fragment 3.

To prepare an initial heavy chain expression vector, plasmid p24BRH was cleaved with ApaI and SacI, and an ApaI/SacI fragment containing IgG4 genomic DNA was isolated. Fragment 3 was ligated to a common ApaI site on the isolated fragment from plasmid p24BRH. A resulting PstI/SacI fragment (encompassing residues 81–121 of the h25D2H-1 variable region joined to IgG4 DNA encoding the complete IgG4 constant region) was then ligated to a Bluescribe plasmid that had previously been cleaved with PstI and SacI, to produce a plasmid designated pAS6.

The IgG4 genomic DNA was then replaced with the cDNA. First, a plasmid containing the IgG4 cDNA inserted between the PstI and NotI sites of the pSV.Sport vector was cleaved at the PstI site in the vector upstream of the cDNA and at a BstEII site within the IgG4 cDNA. This plasmid had been constructed as follows.

Oligonucleotide primers corresponding to the entire heavy chain variable region (VH) of an unrelated humanized antibody were synthesized by standard methods. The designations of these oligonucleotides and the corresponding SEQ ID NOs defining their sequences were as follows:

| Oligonucleotide | SEQ ID NO. |
| --- | --- |
| B2474CC | 43 |
| B2419CC | 44 |
| B2420CC | 45 |
| B2475CC | 46 |
| B2477CC | 47 |
| B2479CC | 48 |

Pairs of oligonucleotides B2474CC and B2419CC, B2420CC and B2475CC, B2477CC and B2479CC were heat-denatured, annealed, and incubated with Taq polymerase or Pfu (Stratagene, La Jolla, Calif.). In the polymerase chain reactions (PCRs), the two oligonucleotides in each pair were complementary to each other by about 24 to 30 nucleotides. Therefore, each oligonucleotide served as the template for the other.

The PCRs were carried out for 18 cycles, after which the three resulting DNA fragments, corresponding to the three consecutive segments of VH, designated VH1, VH2 and VH3, were electrophoresed in an agarose gel and purified by electroelution.

The relative order of the three VH DNA fragments, restriction sites for cloning, and the multicloning-site map of cloning vector used, pSV.Sport, were as follows:

| Fragment | Restriction Sites | PCR Primers |
| --- | --- | --- |
| $V_H 1$ | EcoRI_SpeI | B2474CC + B2419CC |
| $V_H 2$ | SpeI_XbaI | B2420CC + B2475CC |
| $V_H 3$ | EcoRI/XbaI_SalI/ApaI/SstI | B2477CC + B2479CC |

Multi-cloning Sites of pSY.Sport

PstI/KpnI/RsrII/EcoRI/SmaI/SalI/SstI/SpeI/NotI/XbaI/BamHI/HindIII/SnaBI/MluI

Fragment VH1 was restricted with enzymes EcoRI and SpeI and cloned into vector pSV.Sport. Fragment VH2 was subsequently joined to VH1 in pSV.Sport by directional insertion at SpeI and XbaI sites. Fragment VH3 was separately cloned into pSV.Sport as an EcoRI/XbaI-SalI/ApaI/SstI fragment. The three fragments were verified by DNA sequencing.

Full-length VH cDNA of the unrelated antibody was assembled by first joining VH3 to a genomic DNA of the γ4 H-chain constant region (CH) and then attaching the VH3-CH fragment to the VH1-VH2 fragment, as is described more fully below.

To facilitate synthesis and secretion of the heavy chain, a coding sequence for a leader peptide was inserted into the DNA. The amino acid and nucleotide sequences of this leader are those of the leader of the anti-CAMPATH-1 antibodies (Reichmann et al., supra).

To construct DNA encoding a full-length antibody H-chain, the VH synthetic cDNA was combined with human γ4 constant-region genomic DNA (ATCC 57413) using ApaI restriction cleavage and ligation. This procedure was initiated by digesting plasmid pSV.Sport containing VH3 with NotI followed by treatment with Klenow DNA polymerase (Boehringer Mannheim) to generate blunt ends. The resulting DNA was ethanol-precipitated, resuspended, and digested with ApaI. This restricted plasmid DNA was ligated with the ApaI/SmaI restriction fragment of the genomic γ4 constant region.

The VH3-CH genomic DNA was then excised as an XbaI/HindIII fragment and inserted into pSV.Sport already containing VH1-VH2, thereby completing assembling of the full-length heavy chain DNA.

In subsequent manipulations, a human γ4 constant-region cDNA was designed and constructed to replace the genomic DNA. This was accomplished using six oligonucleotide PCR primers that were synthesized by standard methods. The designations of these oligonucleotides and the corresponding SEQ ID NOs defining their sequences were as follows:

| Oligonucleotide | SEQ ID NO. |
| --- | --- |
| B2491CC | 49 |
| B2498CC | 50 |
| B2499CC | 51 |
| B2597CC | 52 |
| B2598CC | 53 |
| B2656CC | 54 |

Primers B2491CC, B2499CC and B2598CC corresponded to the plus strand of γ4 constant region cDNA. Primers B2498CC, B2597CC and B2656CC corresponded to the minus strand. Using human γ4 genomic DNA as the template, three consecutive double-stranded DNA fragments encompassing the entire γ4 constant-region coding cDNA were generated by PCR.

The three CH DNA segments, restriction sites for cloning, and primers used were as follows:

| Segment | Restriction Sites | PCR Primers |
| --- | --- | --- |
| CH A. | SalI_EcoRI | B2491CC + B2498CC |
| CH B. | EcoRI_XhoI/SalI | B2499CC + B2500CC |
| CH C. | SalI/XhoI_NotI | B2598CC + B2656CC |

Segment A was cloned into pUC19 as a SalI/EcoRI restriction fragment. Segment C, as a SalI/XhoI-NotI restriction fragment, was cloned into pSV.Sport. Segment B, as an EcoR1-XhoI/SalI fragment, was cloned into pSV.Sport already containing segment C. All three segments were verified by DNA sequencing.

The 65 4 cDNA was assembled by excising segment A with PstI and EcoRI, and cloning this fragment into pSV.Sport already containing segments B and C. The restriction map of the human γ4 CH cDNA and its relative position in pSV.Sport multi-cloning sites are as follows:

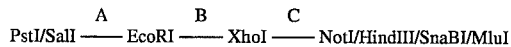

The γ4 CH cDNA was excised as a SalI—HindIII fragment to replace the genomic γ4 fragment in the previously described full-length H-chain construct. The final product was the pSVSPORT-1 vector that was cleaved as described above.

Next, plasmid pAS6 was linearized with PstI and partially digested with BstEII within the IgG4 sequence. A fragment containing a segment of the coding sequences of the variable region from the PstI site (amino acid residues 81–121) and the IgG4 cDNA to the BstEII site (residues 122–191) was isolated and subcloned into the pSV.Sport containing the IgG4 cDNA, between the PstI and BstEII sites. The construct, designated pAS7, encompassed residues 81–121 of the variable region joined to the entire IgG4 cDNA flanked by a 5′ PstI site and a 3′ XbaI site.

Plasmid pAS7 was cleaved with PstI and XbaI, and the fragment (containing residues 81–121 of the variable region and the IgG4 constant region cDNA) was subcloned into vector pBS1-2 (containing fragment 1-2) between the PstI and XbaI sites. This vector, designated pDA5, was then linearized with SacI and treated with T4 DNA polymerase under conditions that left flush ends. The entire coding region of the h25D2H-1 heavy chain was isolated after SalI digestion and ligated to vector pSRS, which had previously been cleaved with SalI and SmaI. The final plasmid was designated pSh25D2H-1.

Four variants of the h25D2H-1 heavy chain (designated h25DH-2 through h25D2H-5) were constructed. The amino acid changes incorporated into the four variants are indicated in FIG. 1, in which amino acid residues are shown using standard single-letter abbreviations, and the sequences within CDRs 1, 2 and 3 of antibody 25D2 and the variants are aligned with those of antibody LAY. Residues not shown were those of the corresponding position in antibody LAY.

The sequence identification numbers of the amino acid sequences within CDRs 1, 2 and 3 of antibody LAY, antibody 25D2, humanized heavy chain h25D2H-1 and variants thereof (see FIG. 1) are as follows:

CDR1
  LAY (SEQ ID NO: 80)
  25D2 (SEQ ID NO: 83)
  h25D2H-1 (SEQ ID NO: 83)
  h25D2H-2 (SEQ ID NO: 86)
  h25D2H-3 (SEQ ID NO: 87)
  h25D2H-4 (SEQ ID NO: 87)
  h25D2H-5 (SEQ ID NO: 86)

CDR2
  LAY (SEQ ID NO: 81)
  25D2 (SEQ ID NO: 84)
  h25D2H-1 (SEQ ID NO: 84)
  h25D2H-2 (SEQ ID NO: 84)
  h25D2H-3 (SEQ ID NO: 84)
  h25D2H-4 (SEQ ID NO: 88)
  h25D2H-5 (SEQ ID NO: 88)

CDR3
  LAY (SEQ ID NO: 82)
  25D2 (SEQ ID NO: 85)
  h25D2H-1 (SEQ ID NO: 85)
  h25D2H-2 (SEQ ID NO: 85)
  h25D2H-3 (SEQ ID NO: 85)
  h25D2H-4 (SEQ ID NO: 85)
  h25D2H-5 (SEQ ID NO: 85).

All of the additional heavy chain variants were constructed by replacing DNA restriction endonuclease fragments from plasmid pDA5 with double-stranded oligonucleotide cassettes containing the desired mutations. In each cassette, the nucleotide sequences chosen to encode the protein sequence maintained the codons that were used in the original version, except that some codons were altered to incorporate the amino acid changes and also to introduce a unique restriction endonuclease cleavage site for selection of positive transformants.

To construct h25D2H-2, an oligonucleotide cassette comprising oligonucleotides designated 3112 (SEQ ID NO: 55) and 3116 (SEQ ID NO: 56) containing a "silent" NheI site was used to replace the BamHI/SmaI DNA fragment in pDA5, and the new plasmid was designated pKM21. To create h25D2H-3, the DNA of pKM21 was cleaved with NheI and SmaI, releasing CDR 1. This NheI/SmaI CDR 1 DNA fragment was then replaced with an oligonucleotide cassette comprising oligonucleotides 3117 (SEQ ID NO: 57) and 3118 (SEQ ID NO: 58), to generate pKM23 containing the h25D2H-3 sequence.

Vectors pKM21 and pKM23 were cleaved with SalI and SmaI, and the fragments containing the altered CDR 1 sequences were isolated and subsequently used to replace the corresponding CDR 1 DNA fragment in vector pSh25H-1. The resulting expression vectors encoding the h25D2H-2 and h25D2H-3 heavy chains were designated pSh25H-2 and pSh25H-3, respectively.

To construct the h25D2H-4 coding sequence, plasmid pKM23 was cleaved with MscI and PstI to release a DNA fragment encompassing CDR 2. Plasmid pKM21 was similarly prepared with MscI and PstI to construct the h25D2H-5 coding sequence. An oligonucleotide cassette comprising oligonucleotides 3119 (SEQ ID NO: 59) and 3120 (SEQ ID NO: 60) encompassing the altered CDR 2 was inserted between the MscI and PstI sites in both plasmids, to generate h25D2H-4 and h25D2H-5, respectively.

The resulting plasmids were digested with SacI and treated with T4 DNA polymerase under conditions that left flush ends. The coding regions for the h25D2H-4 and h25D2H-5 heavy chains were isolated following SalI cleavage and subcloned into vector pSRS which had previously been digested with SalI and SmaI. The final vectors were designated pSh25H-4 and pSh25H-5, respectively.

Expression and Purification of the Humanized Antibodies

All of the humanized antibody DNAs were transfected into COS 7 cells by electroporation, and the medium was replaced with serum-free medium four hours after transfection. The cells were propagated in serum-free medium for 3 days, after which the medium was harvested. To obtain greater amounts of the humanized antibodies, stable CHO cell lines were established that produced the h25D2-1 and the h25D2-4 antibodies.

The appropriate heavy chain plasmid (pSh25H-1 and pSh25H-4, respectively) was co-transfected with the pKM20 light chain plasmid at a ratio of 10:1 into CHO DXB11 cells. Of approximately 40 clones selected for resistance to hypoxanthine and thymidine starvation, greater than 50% tested positive for h25D2-1 antibody expression in a human IgG4 ELISA assay.

Twelve of the clones producing the greatest amount of antibody h25D2-1 were subjected to methotrexate-mediated DNA amplification. Six of these clones (designated h25D2-1 #1, #7, #15, #17, #18 and #21) were selected for growth in the presence of 100–250 nM methotrexate. The levels of antibodies expressed by these clones was estimated based on ELISA to be about 200–700 ng/$10^6$ cells/day. Clone #17 clone was expanded into roller bottle culture to obtain greater quantities of the h25D2-1 antibody for purification and characterization.

Approximately 40 clones transfected with the h25D2-4 plasmids were also selected for resistance to hypoxanthine and thymidine starvation. About 30% of these clones tested positive for antibody expression in a human IgG4 ELISA assay. The positive clones were grown in the presence of 5 nM methotrexate. The antibody level of one of the h25D2-4 clones (designated clone #7A) was estimated by IgG4 ELISA to be about 50–100 ng/$10^6$ cells/day. This clone was expanded into roller bottle culture to produce greater quantities of antibody h25D2-4 for purification and characterization.

Serum-free conditioned medium containing antibodies produced by CHO cell clones in roller bottle culture was harvested continuously as described above. Antibodies in the conditioned medium were partially purified by protein G-SEPHAROSE® chromatography. Analysis of the antibodies by reducing SDS-PAGE showed a high degree of purity (at least about 90%). Analysis of the antibodies by a series of ELISA assays that showed that they contained both human k and γ4 constant regions.

Example III

Antibody Characterization

Affinity Constants

All five variants of the humanized heavy chain gene were independently co-transfected into COS 7 cells with the pKM20 light chain vector. The serum-free conditioned medium was harvested after 72 hours and concentrated. Affinity constants were determined as described above, with the results shown in Table 3.

TABLE 3

| Antibody | Source* | Coating Antibody | Apparent $K_d$ |
|---|---|---|---|
| h25D2-1 | COS CM | α hIgG4 Fc | 4 nM |
| h25D2-2 | COS CM | α hIgG4 Fc | 29 nM |
| h25D2-3 | COS CM | α hIgG4 Fc | 5 nM |
| h25D2-4 | COS CM | α hIgG4 Fc | 5 nM |
| h25D2-5 | COS CM | α hIgG4 Fc | 31 nM |
| 25D2 | Purified | α rat IgG Fc | 1 nM |

*COS CM = COS cell conditioned medium.

As shown in Table 3, the affinities of humanized antibodies h25D2-1, h25D2-3 and h25D2-4 for binding to human IL-4 were similar to that of the native rat 25D2 antibody. The affinities of antibodies h25D2-2 and h25D2-5 antibodies were lower.

Competitive Binding Analysis

To further characterize humanized antibody variants h25D2-1 and h25D2-4, competitive binding assays with the humanized antibodies and rat antibody 25D2 were performed as described above. The results showed that at room temperature antibody h25D2-1 was 3-fold less effective than antibody 25D2 in competing with antibody 25D2 for binding to $^{125}$I-hIL-4. Antibody h25D2-4 was about 100-fold less effective than antibody 25D2 in the same assay. When the same assays were carried out at 4° C., however, humanized antibody h25D2-1 was as effective in the competition assay as the native antibody, and antibody h25D2-4 was only 2-fold less effective.

Receptor Binding Inhibition

Humanized antibodies h25D2-1 and h25D2-4 antibodies were assayed as described above for the ability to inhibit binding of radiolabeled hIL-4 to recombinant hIL-4 receptors expressed on the Jijoye CJ cell line. With a constant concentration of the radiolabeled hIL-4, the concentration of antibodies h25D2-1 and h25D2-4 required to cause 50% inhibition of receptor binding ($IC_{50}$) was calculated to be 0.5–1.0 and 1.0–2.0 nM, respectively. The $IC_{50}$ for the native 25D2 antibody was determined to be 0.5–1.0 nM.

Inhibition of Germline Epsilon Promoter Activity

Jijoye C12 cells contain multiple endogenous copies of a human growth hormone reporter gene operably linked to a germline ε transcript promoter. This promoter is inducible by IL-4 [Rothman et al., J. Exp. Med. 168:2385 (1988)].

To determine whether antibodies h25D2-1 and h25D2-4 could block induction by human IL-4 of the germline ε promoter, assays were carried out using Jijoye C12 cells as described above. $IC_{50}$ values for antibodies h25D2-1 and h25D2-4 were found to be about 120 and 600 pM, respectively, compared to a range of 20–40 pM observed for wild-type antibody 25D2.

Example IV

High Affinity Humanized Antibodies

Strategy

The light and heavy chains of humanized antibody h25D2-1 described above were selected for further modification to construct a markedly superior humanized monoclonal antibody designated h25D2-9. The light and heavy chains of the starting antibody are designated above as h25D2L-1 and h25D2H-1, respectively, and will be referred to as such below.

Initially, humanized antibody versions designated h25D2-7 and h25D2-8 were designed that contained inter alia a modification of heavy chain h25D2H-1 in which the alanine residue at position 97 (see SEQ ID NO: 32) was replaced with a valine residue present in the rodent antibody at that position. This modified heavy chain in versions h25D2-7 and h25D2-8 was combined with light chains h25D2L and h25D2L-1, respectively. The desired performance characteristics, however, were not obtained with these antibodies.

To make antibody h25D2-9, the framework regions of the parental LAY heavy and light chain sequences were inspected for residues differing from the human consensus residues for the heavy chain subgroup III and kappa light chain subgroup I, as defined by Kabat, supra.

This analysis differed from the method employed by Adair et al. (International Patent Application Publication No.WO 91/09967) in that (a) all positions at which the sequence had been altered to the rodent residue to form h25D2-1 were excluded from further consideration, and (b) consensus subgroup residues were considered instead of overall consensus residues.

Using information obtained from the framework sequence inspections, humanized antibody h-25D2-9 was designed by changing several of the non-consensus h25D2-1 residues to either the corresponding 25D2 rodent antibody residue or to the human consensus residue, employing the method of Adair et al., supra, modified as described above. Nine heavy and five light chain residues of antibody h25D2-1 were thus changed in the design of antibody h25D2-9.

A summary of the changes made, including the relevant Kabat positions and residues in the various constructs, antibody LAY and the original rodent antibody 25D2, is shown in Table 4.

TABLE 4

| Kabat No. | h25D2-9 | h25D2-9 Rationale | h25D2-1 | 25D2 | LAY | Subgroup Human Consensus |
|---|---|---|---|---|---|---|
| Heavy Chain Variable Domain | | | | | | |
| 1 | E | Rodent | E | E | A | E |
| 5 | V | Consensus | L | V | L | V |
| 49 | A | Rodent | A | A | A | S |
| 72 | D | Rodent | D | D | N | D |
| 82B | S | Consensus | G | S | G | S |
| 83 | R | Consensus | Q | R | Q | R |
| 86 | D | Consensus | V | D | V | D |
| 87 | T | Rodent | S | T | S | T |
| 89 | V | Consensus | I | T | I | V |
| Light Chain Variable Domain | | | | | | |
| 13 | A | Consensus | V | A | V | A |
| 42 | K | Consensus | L | E | L | K |
| 73 | L | Consensus | F | L | F | L |
| 83 | F | Consensus | I | V | I | F |
| 106 | I | Consensus | V | L | V | I |

Standard single-letter abreviations are used to represent the amino acid residues.

The rationale for inclusion of human consensus or rodent is also provided in Table 4. Note that four heavy chain (Kabat positions 1, 49, 72, and 87) and no light chain residues were included as rodent. Five heavy chain (Kabat positions 5, 82B, 83, 86, and 89) and five light chain (Kabat positions 13, 42, 73, 83, and 106) residues were included as human consensus. At heavy chain positions 1, 5, 72, 82B, 83, 86, and 87 and light chain positions 13 and 73, rodent and human consensus residues were identical. The rationale for inclusion in h25D2-9 was consensus for all of these positions, with the exception of heavy chain positions 1, 72, and 87, which were included as rodent.

Construction

Light Chain A Bluescribe plasmid containing the EcoRI/ KpnI fragment 1 (used in the construction of light chain h25D2L described above) inserted between the EcoRI and KpnI sites served as the starting plasmid. Four oligonucleotide cassettes comprising eight paired synthetic oligonucleotides were consecutively inserted into the vector to generate a plasmid designated h25D2-9 $V_L$.

The designations of these oligonucleotides (shown paired as in the cassettes), followed in parentheses by the corresponding sequence identification numbers, were as follows:

3866 (SEQ ID NO: 61)
3867 (SEQ ID NO: 62)
3944 (SEQ ID NO: 63)
3945 (SEQ ID NO: 64)
3966 (SEQ ID NO: 65)
3967 (SEQ ID NO: 66)
3979 (SEQ ID NO: 67)
3980 (SEQ ID NO: 68)

During the construction, silent restriction endonuclease cleavage sites were added to the cassettes for identification of recombinant plasmids. Initially, an EcoRI/BstEII fragment in the starting plasmid was replaced with the cassette comprising oligonucleotide pair 3866/3867. The result was replacement of the valine residue at position 13 of light chain h25D2-1 (see SEQ ID NO: 27) with an alanine residue and introduction of a silent HindIII site, and the construct was designated pKM45.

Next, the cassette comprising oligonucleotide pair 3944/ 3945 was inserted between the KpnI and XbaI sites of pKM45. The resulting construct, designated pKM47, contained a lysine residue at position 42 instead of the leucine residue present at that position in light chain h25D2L-1 and a silent XhoI site.

The casette comprising oligonucleotide pair 3966/3967 was then inserted between the XbaI and PstI sites of pKM47 to generate pKM49 which contained a leucine residue at position 73 instead of the phenylalanine present at that position in light chain h25D2L-1, and a silent XmnI site.

Finally, cassette comprising oligonucleotide pair 3979/3980 was inserted between the PstI and SphI sites of pKM49 to yield pKM50. Plasmid pKM50 contained a phenylalanine residue at position 83 instead of the isoleucine residue at that position in h25D2L-1, and a silent SnaBI site. It also contained an MscI site to facilitate further cloning manipulations.

The construct was further modified to contain an isoleucine residue at position 105, instead of the valine residue present at that position in h25D2L-1. To make this change, the Bluescript vector containing the h25D2L-1 coding sequence was subjected to single-stranded mutagenesis (Sambrook et al., 1989, in *Molecular Cloning*; Cold Spring Harbor Press; Vol. I p. 4.48 and Vol. II p. 15.63–15.65) using an oligonucleotide designated 3974 (sequence defined by SEQ ID NO: 69). This oligonucleotide produced the desired substitution and resulted in deletion of two StyI sites, thereby facilitating selection of the mutant plasmids. The resulting plasmid was designated pKM51.

The SalI-MscI fragment of pKM51 was replaced with the corresponding fragment from pKM50 to yield plasmid pKM52. This plasmid contained the entire coding region of the h25D2-9 light chain and included, in summary, the following changes with respect to the h25D2-1 light chain: V13A, L42K, F73L, I83F, and V105I.

The complete light chain variable region sequence is shown in SEQ ID NO: 70 of the Sequence Listing, together with the sequence of a secretory leader.

To construct a mammalian expression vector, plasmid pKM52 containing the h25D2-9 light chain sequence was cleaved at the 3' end with SpeI and treated with the Klenow fragment of DNA polymerase under conditions that left flush ends. The h25D2-9 DNA fragment was obtained after cleavage at the 5' end with SalI and was ligated to vector pDSRS which had previously been digested with SalI and SmaI. The completed expression vector, designated pKM53, contained the entire coding region for the h25D2L-9 light chain, including the signal peptide and human kappa constant region.

Heavy Chain

Beginning with plasmid pDA5 described above, heavy chain h25D2-1 of antibody h25D2-1 (see SEQ ID NO: 32) was modified by restriction cleavage and the successive introduction of four oligonucleotide cassettes which comprised eight paired synthetic oligonucleotides. Silent restriction endonuclease cleavage sites were added to the cassettes for identification of recombinant plasmids.

The designations of these oligonucleotides (shown paired as in the casettes), followed in parentheses by the corresponding sequence identification numbers, were as follows:

3592 (SEQ ID NO: 71)
3593 (SEQ ID NO: 72)
3850 (SEQ ID NO: 73)
3851 (SEQ ID NO: 74)
3711 (SEQ ID NO: 75)
3712 (SEQ ID NO: 76)
3848 (SEQ ID NO: 77)
3849 (SEQ ID NO: 78)

Modification of the heavy chain h25D2-1 of antibody h25D2-1 was initiated by replacing the MscI/PstI fragment of pDA5 with a cassette comprising oligonucleotide pair 3592/3593. This incorporated an N73D and N77S change, as well as a silent XbaI site. The resulting plasmid was designated pKM37. A SalI/KpnI fragment (encompassing amino acid residues 1–113) was isolated from pKM37 and subcloned into a Bluescript vector, to facilitate further cloning manipulations. This vector was designated pKM39.

The oligonucleotide cassette comprising oligonucleotide pair 3850/3851 was inserted between the BamHI and SacII sites (SacII located in vector) of pKM39. The resulting plasmid, termed pKM44, contained L5V, N73D and N77S changes.

Plasmid pKM39 served as the starting plasmid for incorporation of the last two cassettes. Initially, a SmaI fragment encompassing a PstI site in the vector was removed from pKM39 to facilitate cloning. The cassette comprising oligonucleotide pair 3711/3712 was used to replace the corresponding fragment in the $V_H$ region of the vector. The final construct was designated pKM41 and contained the A97V change and a silent NruI site that was used in subsequent cloning mainpulations.

Next, the cassette comprising oligonucleotide pair 3848/3849 was inserted between the PstI and NruI sites of pKM41. The resulting construct, designated pKM43, contained an A97V change as well as G85S, Q87R, V90D, S91T and I93V changes. The KpnI/MscI fragment of pKM43 was isolated and used to replace the corresponding fragment of pKM44 (pKM44 contained the N73D, N77S and L5V changes). The resulting plasmid, designated pKM46, contained the complete h25D2-9 $V_H$ region.

The complete heavy chain variable region sequence is shown in SEQ ID NO: 79 of the Sequence Listing, together with the sequence of a secretory leader.

A SalI/KpnI fragment (encompassing amino acid residues 1–113 of the heavy chain) served to replace the corresponding fragment in the pSh25D2H-1 expression vector, and the final expression vector for the h25D2-9 heavy chain was designated pSh25D2H-9.

Antibody Expression Levels

COS cells were transfected as described above with 10 μg each of either plasmids pKM53 (for antibody h25D2-9 light chain) and pSh25D2H-9 (for antibody h25D2-9 heavy chain) or plasmids pKM20 (for antibody h25D2-1 light chain) and pSh25D2H-1 (for antibody h25D2-1 heavy chain). Following a four-day incubation in medium containing 1% fetal calf serum to permit antibody secretion, samples of medium from the COS cells were subjected to ELISA essentially as described above to determine the levels of expression of humanized antibodies h25D2-1, the best of the prior humanized antibodies in terms of performance characteristics, and h25D2-9.

It was thereby found that humanized antibody h25D2-1 was produced at a level of 10–20 ng/ml of medium. In contrast, antibody h25D2-9 was produced at a level of 100 ng/ml, a five to ten fold increase over that of h25D2-1.

Competition Assay

A plate competition assay was carried out as described above using $^{125}$I-hIL-4, immobilized rat antibody 25D2, and varying levels of free antibodies 25D2, h25D2-1 or h25D2-9. The results of this assay, which was carried out both at 4° C. and at room temperature (about 22° C.), are shown in Fifure 2.

As can be seen from FIG. 2, both humanized antibodies were about as effective as rodent antibody 25D2 in competing for binding to the $^{125}$I-hIL-4 at 4° C. At room temperature, however, a concentration of antibody h25D2-1 that was more than twice that of antibody h25D2-9 was required to produce a comparable, fifty percent inhibition of the binding of the $^{125}$I-hIL-4 to the immobilized antibody. Thus antibody h25D2-1 was less active than antibody h25D2-9 at the higher temperature.

Bioassay

Figure 3:
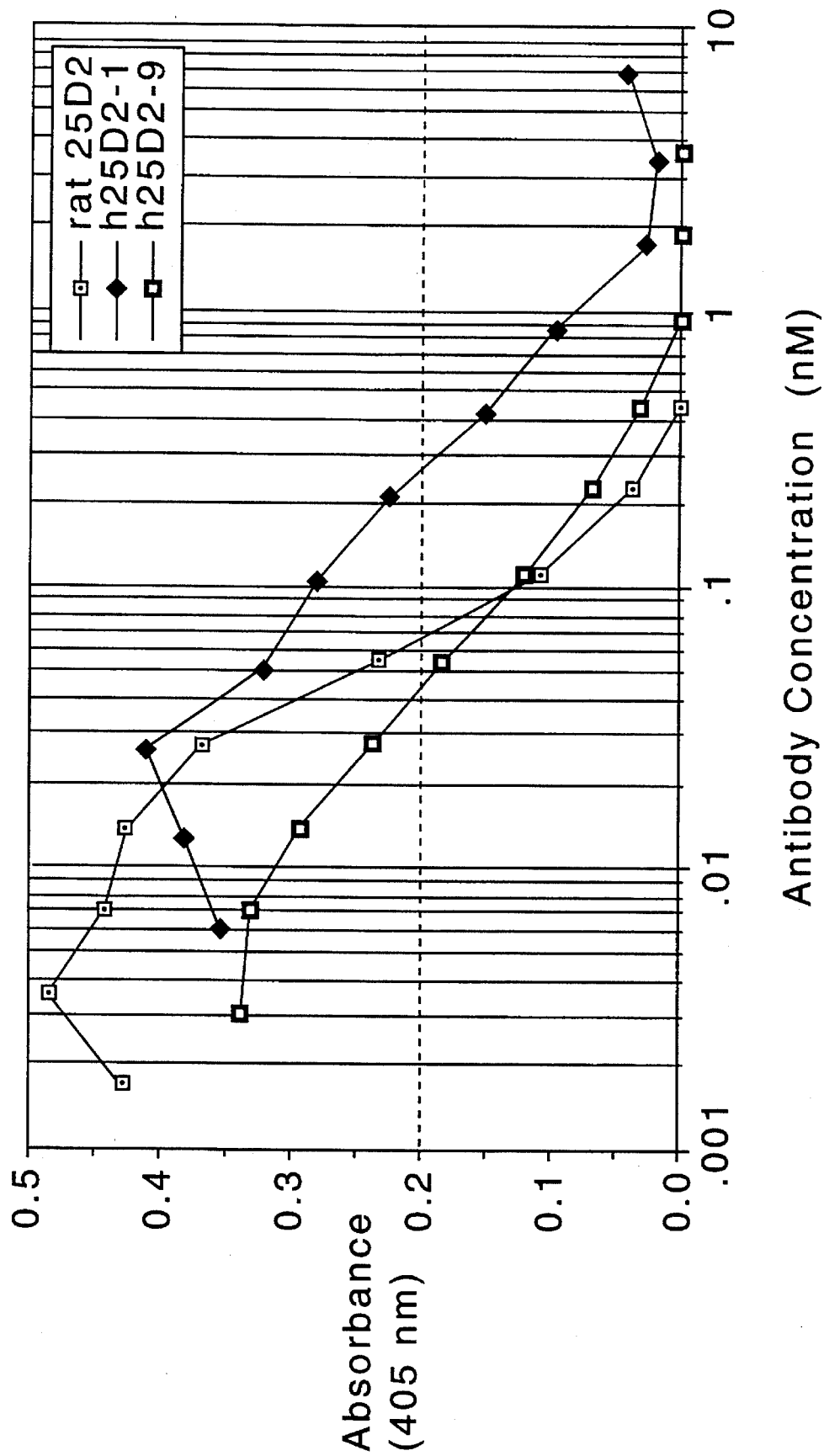
FIG. 3 is a graphical representation of the results of a bioassay in which the effects of varying concentrations of the indicated antibodies on the response of a Jijoye cell line to a fixed concentration of human IL-4 were measured by ELISA. Absorbance at 405 nM is shown as a function of antibody concentration.

To compare the abilities of rodent antibody 25D2 and humanized antibodies h25D2-1 and h25D2-9 to inhibit induction of human growth hormone in the germline epsilon reporter assay, the assay employing the Jijoye C12 cell line described above was carried out on varying amounts of all three antibodies. The results are shown in FIG. 3, where it is evident that although the 25D2 and h25D2-9 antibodies were similar in activity. In contrast, an approximately five-fold higher concentration of antibody h25D2-1 was required to produce a comparable, fifty percent inhibition in the assay.

Hybridoma Deposit

Hybridoma MP4.25D2.11 was deposited Sep. 1, 1988 with the American Type Culture Collection, Rockville, Md., USA (ATCC), under accession number ATCC HB 9809. This deposit was made under conditions as provided under ATCC's agreement for Culture Deposit for Patent Purposes, which assures that the deposit will be made available to the US Commissioner of Patents and Trademarks pursuant to 35 USC 122 and 37 CFR 1.14 and will be made available to the public upon issue of a U.S. patent and requires that the deposit be maintained. Availability of the deposited strain is not to be construed as a license to practise the invention in contravention of the rights granted under the authority of any government in accordance with its patent laws.

Many modifications and variations of this invention can be made without departing from its spirit and scope, as will become apparent to those skilled in the art. The specific embodiments described herein are offered by way of example only, and the invention is to be limited only by the terms of the appended claims.

---

What is claimed is:

1. A polypeptide comprising an amino acid sequence shown in SEQ ID NO: 70 or SEQ ID NO: 79, which sequences correspond, respectively, to a light chain and heavy chain variable region of a humanized monoclonal antibody that specifically binds to human IL-4.

2. A humanized monoclonal antibody or fragment thereof which specifically binds human IL-4 comprising a polypeptide of claim 1.

3. An antibody of claim 2 which is antibody h25D2-9.

4. A nucleic acid which encodes a polypeptide comprising an amino acid sequence shown in SEQ ID NO: 70 or SEQ ID NO: 79, which sequences correspond, respectively, to a light chain and heavy chain variable region of a humanized monoclonal antibody that specifically binds to human IL-4.

5. A recombinant vector comprising a nucleic acid of claim 4.

6. A recombinant vector of claim 5 which is plasmid pKM53 or pSh25D2H-9.

7. A host cell comprising a recombinant vector of claim 5.

8. A host cell of claim 7 which is a COS cell.

9. A host cell of claim 8 which comprises plasmid pKM53 or pSh25D2H-9.

10. A method for making a polypeptide comprising culturing a host cell of claim 7 under conditions in which the nucleic acid is expressed.

11. The method of claim 10 in which the host cell is a COS cell.

12. The method of claim 11 in which the host cell comprises plasmid pKM53 or pSh25D2H-9.

* * * * *

SEQUENCE LISTING ( 1 ) GENERAL INFORMATION:

( i i i ) NUMBER OF SEQUENCES: 88

( 2 ) INFORMATION FOR SEQ ID NO: 1:

( i ) SEQUENCE CHARACTERISTICS:
        ( A ) LENGTH: 363 base pairs
        ( B ) TYPE: nucleic acid
        ( C ) STRANDEDNESS: double
        ( D ) TOPOLOGY: linear ( x i ) SEQUENCE DESCRIPTION: SEQ ID NO: 1:

```
GAA  CTG  CAG  TTG  GTA  GAA  AGT  GGG  GGA  GGT  CTG  GTG  CAG  CCT  GGA  AGG    48
Glu  Leu  Gln  Leu  Val  Glu  Ser  Gly  Gly  Gly  Leu  Val  Gln  Pro  Gly  Arg
               5                        10                       15

TCT  CTG  AAA  CTA  TCC  TGT  GTG  GCC  TCT  GGA  TTC  TCA  TTC  AGA  AGT  TAC    96
Ser  Leu  Lys  Leu  Ser  Cys  Val  Ala  Ser  Gly  Phe  Ser  Phe  Arg  Ser  Tyr
               20                       25                       30

TGG  ATG  ACC  TGG  GTC  CGT  CAG  GCT  CCA  GGG  AAG  GGG  CTG  GAG  TGG  ATT   144
Trp  Met  Thr  Trp  Val  Arg  Gln  Ala  Pro  Gly  Lys  Gly  Leu  Glu  Trp  Ile
          35                            40                       45

GCA  TCC  ATT  AGT  ATT  TCT  GGT  GAT  AAC  ACG  TAC  TAT  CCA  GAC  TCT  GTG   192
Ala  Ser  Ile  Ser  Ile  Ser  Gly  Asp  Asn  Thr  Tyr  Tyr  Pro  Asp  Ser  Val
     50                       55                            60

AGG  GGC  CGA  TTC  ACT  ATC  TCC  AGG  GAT  GAT  GCA  AAA  AGC  ATC  CTA  TAC   240
Arg  Gly  Arg  Phe  Thr  Ile  Ser  Arg  Asp  Asp  Ala  Lys  Ser  Ile  Leu  Tyr
65                       70                       75                       80

CTT  CAA  ATG  AAC  AGT  CTG  AGG  TCT  GAG  GAC  ACG  GCC  ACT  TAT  TAC  TGT   288
Leu  Gln  Met  Asn  Ser  Leu  Arg  Ser  Glu  Asp  Thr  Ala  Thr  Tyr  Tyr  Cys
                         85                       90                       95

GTA  AGA  GAT  CCC  TAT  TAC  TTC  AGT  GGC  CAC  TAC  TTT  GAT  TTC  TGG  GGC   336
Val  Arg  Asp  Pro  Tyr  Tyr  Phe  Ser  Gly  His  Tyr  Phe  Asp  Phe  Trp  Gly
                    100                      105                      110

CAA  GGA  GTC  ATG  GTC  ACA  GTC  TCC  TCA                                       363
Gln  Gly  Val  Met  Val  Thr  Val  Ser  Ser
```

115                          120

( 2 ) INFORMATION FOR SEQ ID NO: 2:

( i ) SEQUENCE CHARACTERISTICS:
        ( A ) LENGTH: 321 base pairs
        ( B ) TYPE: nucleic acid
        ( C ) STRANDEDNESS: double
        ( D ) TOPOLOGY: linear ( x i ) SEQUENCE DESCRIPTION: SEQ ID NO: 2:

| GAT | ATC | CAG | ATG | ACA | CAG | AGT | CCT | TCA | CTC | CTG | TCT | GCA | TCT | GTG | GGA | 48 |
| Asp | Ile | Gln | Met | Thr | Gln | Ser | Pro | Ser | Leu | Leu | Ser | Ala | Ser | Val | Gly | |
| | | | | 5 | | | | | 10 | | | | | 15 | | |

| GAC | AGA | GTC | ACT | CTC | AAC | TGC | AAA | GCA | AGT | CAG | AAT | ATT | TAT | AAG | AAT | 96 |
| Asp | Arg | Val | Thr | Leu | Asn | Cys | Lys | Ala | Ser | Gln | Asn | Ile | Tyr | Lys | Asn | |
| | | | 20 | | | | | 25 | | | | | 30 | | | |

| TTA | GCC | TGG | TAT | CAG | CAA | AAG | CTT | GGA | GAA | GCT | CCC | AAG | TTC | CTG | ATT | 144 |
| Leu | Ala | Trp | Tyr | Gln | Gln | Lys | Leu | Gly | Glu | Ala | Pro | Lys | Phe | Leu | Ile | |
| | | 35 | | | | | 40 | | | | | 45 | | | | |

| TTT | AAT | GCA | AAA | AGT | TTG | GAG | ACG | GGC | GTC | CCA | TCA | AGG | TTC | AGT | GGC | 192 |
| Phe | Asn | Ala | Lys | Ser | Leu | Glu | Thr | Gly | Val | Pro | Ser | Arg | Phe | Ser | Gly | |
| | 50 | | | | | 55 | | | | | 60 | | | | | |

| AGT | GGA | TCT | GGC | ACA | GAT | TTC | ACA | CTC | ACA | ATC | AGC | AGC | CTA | CAG | CCT | 240 |
| Ser | Gly | Ser | Gly | Thr | Asp | Phe | Thr | Leu | Thr | Ile | Ser | Ser | Leu | Gln | Pro | |
| 65 | | | | | 70 | | | | | 75 | | | | | 80 | |

| GAA | GAT | GTT | GCC | ACA | TAT | TTC | TGC | CAA | CAA | TAT | TAT | AGC | GGG | TGG | ACG | 288 |
| Glu | Asp | Val | Ala | Thr | Tyr | Phe | Cys | Gln | Gln | Tyr | Tyr | Ser | Gly | Trp | Thr | |
| | | | | 85 | | | | | 90 | | | | | 95 | | |

| TTC | GGT | GGA | GGC | ACC | AAG | CTG | GAA | TTG | AAA | CGG | | | | | | 321 |
| Phe | Gly | Gly | Gly | Thr | Lys | Leu | Glu | Leu | Lys | Arg | | | | | | |
| | | | 100 | | | | | 105 | | | | | | | | |

( 2 ) INFORMATION FOR SEQ ID NO: 3:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 3:

CGATGCACAA GTGCGAT                                                                                  17

( 2 ) INFORMATION FOR SEQ ID NO: 4:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 4:

ATCGCACTTG TGCAT                                                                                    15

( 2 ) INFORMATION FOR SEQ ID NO: 5:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 5:

GCACTAGTTC TAGAAGGCCA AGAGGGGCCA CTGACTCTGG GGTCAT                                                   46

( 2 ) INFORMATION FOR SEQ ID NO: 6:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 6:

```
GCGCGGCCGC  GARYTNCARY  TNGTNGARWS  NGGNGGNGGN  CTNGTNCARC  C                51
```

( 2 ) INFORMATION FOR SEQ ID NO: 7:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 7:

```
GCACTAGTTC  TAGATTGGGT  CTAACACTCA  TTCCTGTTGA  AGCTCTTGAC  G                51
```

( 2 ) INFORMATION FOR SEQ ID NO: 8:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 8:

```
GCGCGGCCGC  GAYATHCARA  TGACNCARAG  YCC                                      33
```

( 2 ) INFORMATION FOR SEQ ID NO: 9:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 9:

```
GGAAGGTCTC  TGAAACTATC                                                       20
```

( 2 ) INFORMATION FOR SEQ ID NO: 10:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 10:

```
AGACAGAGTC  ACTCTC                                                           16
```

( 2 ) INFORMATION FOR SEQ ID NO: 11:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 11:

```
CCTTCAAATG  AAC                                                              13
```

( 2 ) INFORMATION FOR SEQ ID NO: 12:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 12:

GTTCATTTGA AGG                                                                                      13

( 2 ) INFORMATION FOR SEQ ID NO: 13:

( i ) SEQUENCE CHARACTERISTICS:
            ( A ) LENGTH: 18 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 13:

GCCTGAAGAT GTTGCCAC                                                                                 18

( 2 ) INFORMATION FOR SEQ ID NO: 14:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 14:

ATTAACCCTC ACTAAAG                                                                                  17

( 2 ) INFORMATION FOR SEQ ID NO: 15:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 15:

AATACGACTC ACTATAG                                                                                  17

( 2 ) INFORMATION FOR SEQ ID NO: 16:

( i ) SEQUENCE CHARACTERISTICS:
            ( A ) LENGTH: 390 base pairs
            ( B ) TYPE: nucleic acid
            ( C ) STRANDEDNESS: double
            ( D ) TOPOLOGY: linear ( x i ) SEQUENCE DESCRIPTION: SEQ ID NO: 16:

```
GAATTCGCCG CCACC ATG GGA TGG AGC TGT ATC ATC CTC TTC TTG GTA              48
                Met Gly Trp Ser Cys Ile Ile Leu Phe Leu Val
                          -15                         -10

GCA ACA GCT ACA GGT GTC CAC TCC GAT ATC CAG ATG ACC CAG AGC CCA           96
Ala Thr Ala Thr Gly Val His Ser Asp Ile Gln Met Thr Gln Ser Pro
             -5                    1                 5

AGC AGC CTG AGC GTG AGC GTG GGT GAC CGC GTG ACC ATC ACC TGC AAG          144
Ser Ser Leu Ser Val Ser Val Gly Asp Arg Val Thr Ile Thr Cys Lys
         10                15                 20

GCC AGC CAG AAC ATC TAC AAG AAC CTG GCC TGG TAC CAG CAG AAG CCA          192
Ala Ser Gln Asn Ile Tyr Lys Asn Leu Ala Trp Tyr Gln Gln Lys Pro
25                  30                 35                    40

GGC CTG GCC CCA AAG TTC CTG ATC TTC AAC GCC AAG AGC CTG GAG ACC          240
Gly Leu Ala Pro Lys Phe Leu Ile Phe Asn Ala Lys Ser Leu Glu Thr
             45                 50                    55
```

| | | | | | | | | | | | | | | | |
|---|---|---|---|---|---|---|---|---|---|---|---|---|---|---|---|
| GGC | GTG | CCA | TCT | AGA | TTC | AGC | GGC | AGC | GGC | AGC | GGC | ACC | GAC | TTC | ACC | 288
| Gly | Val | Pro | Ser | Arg | Phe | Ser | Gly | Ser | Gly | Ser | Gly | Thr | Asp | Phe | Thr |
| | | | 60 | | | | | 65 | | | | | 70 | | |
| TTC | ACC | ATC | AGC | AGC | CTG | CAG | CCA | GAG | GAC | ATC | GCC | ACC | TAC | TAC | TGC | 336
| Phe | Thr | Ile | Ser | Ser | Leu | Gln | Pro | Glu | Asp | Ile | Ala | Thr | Tyr | Tyr | Cys |
| | | 75 | | | | | 80 | | | | | 85 | | | |
| CAG | CAG | TAC | TAC | AGC | GGC | TGG | ACC | TTT | GGC | CAA | GGC | ACC | AAG | GTG | GAG | 384
| Gln | Gln | Tyr | Tyr | Ser | Gly | Trp | Thr | Phe | Gly | Gln | Gly | Thr | Lys | Val | Glu |
| | 90 | | | | | 95 | | | | | 100 | | | | |
| GTG | AAG | | | | | | | | | | | | | | | 390
| Val | Lys | | | | | | | | | | | | | | |
| 105 | | | | | | | | | | | | | | | |

( 2 ) INFORMATION FOR SEQ ID NO: 17:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 17:

GAACAAAAGC TTGACATCCA GATGACCCAG AGCCCAAGCA GCCTGAGCGT GAGCGTGGGT    60

GACCGCGTGA CC    72

( 2 ) INFORMATION FOR SEQ ID NO: 18:

( i ) SEQUENCE CHARACTERISTICS:
        ( A ) LENGTH: 73 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 18:

GAGCTCGGTA CCAGGCCAGG TTCTTGTAGA TGTTCTGGCT GGCCTTGCAG GTGATGGTCA    60

CGCGGTCACC CAC    73

( 2 ) INFORMATION FOR SEQ ID NO: 19:

( i ) SEQUENCE CHARACTERISTICS:
        ( A ) LENGTH: 105 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 19:

GGTACCGGTC CGGAATTCGC CGCCACCATG GGATGGAGCT GTATCATCCT CTTCTTGGTA    60

GCAACAGCTA CAGGTGTCCA CTCCGATATC CAGATGACCC AGAGC    105

( 2 ) INFORMATION FOR SEQ ID NO: 20:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 20:

CTGCTGGTAC CAGGCCAGGT TCTTGTAGAT GTTCTG    36

( 2 ) INFORMATION FOR SEQ ID NO: 21:

( i ) SEQUENCE CHARACTERISTICS:
        ( A ) LENGTH: 80 base pairs (B) TYPE: nucleic acid
(C) STRANDEDNESS: single
(D) TOPOLOGY: linear (xi) SEQUENCE DESCRIPTION: SEQ ID NO: 21:

TCCCCGGGTA CCAGCAGAAG CCAGGCCTGG CCCCAAAGTT CCTGATCTTC AACGCCAAGA     60

GCCTGGAGAC CGGCGTGCCA     80

(2) INFORMATION FOR SEQ ID NO: 22:

(i) SEQUENCE CHARACTERISTICS:
    (A) LENGTH: 84 base pairs
    (B) TYPE: nucleic acid
    (C) STRANDEDNESS: single
    (D) TOPOLOGY: linear (xi) SEQUENCE DESCRIPTION: SEQ ID NO: 22:

GTCGACCTGC AGGCTGCTGA TGGTGAAGGT GAAGTCGGTG CCGCTGCCGC TGCCGCTGAA     60

TCTAGATGGC ACGCCGGTCT CCAG     84

(2) INFORMATION FOR SEQ ID NO: 23:

(i) SEQUENCE CHARACTERISTICS:
    (A) LENGTH: 68 base pairs
    (B) TYPE: nucleic acid
    (C) STRANDEDNESS: single
    (D) TOPOLOGY: linear (xi) SEQUENCE DESCRIPTION: SEQ ID NO: 23:

ACCATCAGCA GCCTGCAGCC AGAGGACATC GCCACCTACT ACTGCCAGCA GTACTACAGC     60

GGCTGGAC     68

(2) INFORMATION FOR SEQ ID NO: 24:

(i) SEQUENCE CHARACTERISTICS:
    (A) LENGTH: 74 base pairs
    (B) TYPE: nucleic acid
    (C) STRANDEDNESS: single
    (D) TOPOLOGY: linear (xi) SEQUENCE DESCRIPTION: SEQ ID NO: 24:

CAGAGTTTAG AATTCACTCA CGCTTCACCT CCACCTTGGT GCCTTGGCCA AAGGTCCAGC     60

CGCTGTAGTA CTGC     74

(2) INFORMATION FOR SEQ ID NO: 25:

(i) SEQUENCE CHARACTERISTICS:
    (A) LENGTH: 33 base pairs
    (B) TYPE: nucleic acid
    (C) STRANDEDNESS: single
    (D) TOPOLOGY: linear (xi) SEQUENCE DESCRIPTION: SEQ ID NO: 25:

GTCGAATTCT CAACACTCTC CCCTGTTGAA GCT     33

(2) INFORMATION FOR SEQ ID NO: 26:

(i) SEQUENCE CHARACTERISTICS:
    (A) LENGTH: 59 base pairs
    (B) TYPE: nucleic acid
    (C) STRANDEDNESS: single
    (D) TOPOLOGY: linear (xi) SEQUENCE DESCRIPTION: SEQ ID NO: 26:

GTTTTGGCCA AGGCACCAAG GTGGAGGTGA AGACTGTGGC TGCACCATCT GTCTTCATC     59

( 2 ) INFORMATION FOR SEQ ID NO: 27:

( i ) SEQUENCE CHARACTERISTICS:
        ( A ) LENGTH: 393 base pairs
        ( B ) TYPE: nucleic acid
        ( C ) STRANDEDNESS: double
        ( D ) TOPOLOGY: linear ( x i ) SEQUENCE DESCRIPTION: SEQ ID NO: 27:

```
GAATTCGCCG CCACC ATG GGA TGG AGC TGT ATC ATC CTC TTC TTG GTA                48
                Met Gly Trp Ser Cys Ile Ile Leu Phe Leu Val
                    -15                         -10

GCA ACA GCT ACA GGT GTC CAC TCC GAT ATC CAG ATG ACC CAG AGC CCA             96
Ala Thr Ala Thr Gly Val His Ser Asp Ile Gln Met Thr Gln Ser Pro
            -5               1               5

AGC AGC CTG AGC GTG AGC GTG GGT GAC CGC GTG ACC ATC ACC TGC AAG            144
Ser Ser Leu Ser Val Ser Val Gly Asp Arg Val Thr Ile Thr Cys Lys
        10              15                  20

GCC AGC CAG AAC ATC TAC AAG AAC CTG GCC TGG TAC CAG CAG AAG CCA            192
Ala Ser Gln Asn Ile Tyr Lys Asn Leu Ala Trp Tyr Gln Gln Lys Pro
25                  30                  35                  40

GGC CTG GCC CCA AAG CTG CTG ATC TAC AAC GCC AAG AGC CTG GAG ACC            240
Gly Leu Ala Pro Lys Leu Leu Ile Tyr Asn Ala Lys Ser Leu Glu Thr
                45                  50                  55

GGC GTG CCA TCT AGA TTC AGC GGC AGC GGC AGC GGC ACC GAC TTC ACC            288
Gly Val Pro Ser Arg Phe Ser Gly Ser Gly Ser Gly Thr Asp Phe Thr
            60                  65                  70

TTC ACC ATC AGC AGC CTG CAG CCA GAG GAC ATC GCC ACC TAC TAC TGC            336
Phe Thr Ile Ser Ser Leu Gln Pro Glu Asp Ile Ala Thr Tyr Tyr Cys
        75                  80                  85

CAG CAG TAC TAC AGC GGC TGG ACC TTT GGC CAA GGC ACC AAG GTG GAG            384
Gln Gln Tyr Tyr Ser Gly Trp Thr Phe Gly Gln Gly Thr Lys Val Glu
90                  95                  100

GTG AAG CGC                                                                 393
Val Lys Arg
105
```

( 2 ) INFORMATION FOR SEQ ID NO: 28:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 28:

AAGCCAGGCC TGGCCCCAAA GCTGCTGATC TACAACGCC                                  39

( 2 ) INFORMATION FOR SEQ ID NO: 29:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 29:

TGGCTGCAGG CTGCT                                                            15

( 2 ) INFORMATION FOR SEQ ID NO: 30:

( i ) SEQUENCE CHARACTERISTICS:
        ( A ) LENGTH: 45 base pairs
        ( B ) TYPE: nucleic acid ( C ) STRANDEDNESS: single
( D ) TOPOLOGY: linear ( x i ) SEQUENCE DESCRIPTION: SEQ ID NO: 30:

ACCTTTGGCC AAGGCACCAA GGTGGAGGTG AAGCGCACTG TGGCT 45

( 2 ) INFORMATION FOR SEQ ID NO: 31:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( x i ) SEQUENCE DESCRIPTION: SEQ ID NO: 31:

TCTAGAACTA GTGGATCC 18

( 2 ) INFORMATION FOR SEQ ID NO: 32:

( i ) SEQUENCE CHARACTERISTICS:
( A ) LENGTH: 435 base pairs
( B ) TYPE: nucleic acid
( C ) STRANDEDNESS: double
( D ) TOPOLOGY: linear ( x i ) SEQUENCE DESCRIPTION: SEQ ID NO: 32:

```
GTCGACGCCG CCACC ATG GGA TGG AGC TGT ATC ATC CTC TTC TTG GTA            48
                Met Gly Trp Ser Cys Ile Ile Leu Phe Leu Val
                 -15              -15              -10

GCA ACA GCT ACA GGT GTC CAC TCC GAG GTG CAG CTG CTG GAG AGC GGC         96
Ala Thr Ala Thr Gly Val His Ser Glu Val Gln Leu Leu Glu Ser Gly
             -5              1               5

GGC GGC CTG GTG CAG CCA GGC GGA TCC CTG CGC CTG AGC TGC GCC GCC        144
Gly Gly Leu Val Gln Pro Gly Gly Ser Leu Arg Leu Ser Cys Ala Ala
         10              15              20

AGC GGC TTC AGC TTC CGC AGC TAC TGG ATG ACC TGG GTG CGC CAG GCC        192
Ser Gly Phe Ser Phe Arg Ser Tyr Trp Met Thr Trp Val Arg Gln Ala
 25              30              35              40

CCG GGC AAG GGC CTG GAG TGG GTG GCC AGC ATC AGC ATC AGC GGC GAC        240
Pro Gly Lys Gly Leu Glu Trp Val Ala Ser Ile Ser Ile Ser Gly Asp
             45              50              55

AAC ACC TAC TAC CCA GAC AGC GTG CGC GGC CGC TTC ACC ATC AGC CGC        288
Asn Thr Tyr Tyr Pro Asp Ser Val Arg Gly Arg Phe Thr Ile Ser Arg
             60              65              70

AAC GAC AGC AAG AAC ACC CTG TAC CTG CAG ATG AAC GGC CTG CAA GCC        336
Asn Asp Ser Lys Asn Thr Leu Tyr Leu Gln Met Asn Gly Leu Gln Ala
         75              80              85

GAG GTG AGC GCC ATC TAC TAC TGC GCC CGC GAC CCA TAC TAC TTC AGC        384
Glu Val Ser Ala Ile Tyr Tyr Cys Ala Arg Asp Pro Tyr Tyr Phe Ser
     90              95              100

GGC CAC TAC TTC GAC TTC TGG GGC CAG GGT ACC CTG GTG ACC GTG AGC        432
Gly His Tyr Phe Asp Phe Trp Gly Gln Gly Thr Leu Val Thr Val Ser
 105             110             115             120

AGC                                                                    435
Ser
```

( 2 ) INFORMATION FOR SEQ ID NO: 33:

( i ) SEQUENCE CHARACTERISTICS:
( A ) LENGTH: 84 base pairs
( B ) TYPE: nucleic acid
( C ) STRANDEDNESS: single
( D ) TOPOLOGY: linear ( x i ) SEQUENCE DESCRIPTION: SEQ ID NO: 33:

```
ACTAGTGAAT TCGTCGACGC CGCCACCATG GGATGGAGCT GTATCATCCT CTTCTTGGTA      60

GCAACAGCTA CAGGTGTCCA CTCC                                            84
```

( 2 ) INFORMATION FOR SEQ ID NO: 34:

( i ) SEQUENCE CHARACTERISTICS:
        ( A ) LENGTH: 84 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 34:

```
GCAGCTCAGG CGCAGGGATC CGCCTGGCTG CACCAGGCCG CCGCCGCTCT CCAGCAGCTG      60

CACCTCGGAG TGGACACCTG TAGC                                            84
```

( 2 ) INFORMATION FOR SEQ ID NO: 35:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 35:

```
AGCGTCGACG CCGCCACCAT G                                               21
```

( 2 ) INFORMATION FOR SEQ ID NO: 36:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 36:

```
GTATCCCCCG GGGCCTGGCG CACCCAGGTC ATCCAGTAGC TGCGGAAGCT GAAGCCGCTG      60

GCGGCGCAGC TCAGGCGCAG                                                 80
```

( 2 ) INFORMATION FOR SEQ ID NO: 37:

( i ) SEQUENCE CHARACTERISTICS:
        ( A ) LENGTH: 79 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 37:

```
GTATCCCCCG GGCAAGGGCC TGGAGTGGGT GGCCAGCATC AGCATCAGCG GCGACAACAC      60

CTACTACCCA GACAGCGTG                                                  79
```

( 2 ) INFORMATION FOR SEQ ID NO: 38:

( i ) SEQUENCE CHARACTERISTICS:
        ( A ) LENGTH: 78 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 38:

```
GTAGAACTGC AGGTACAGGG TGTTCTTGCT GTCGTTGCGG CTGATGGTGA AGCGGCCGCG      60

CACGCTGTCT GGGTAGTA   78
```

( 2 ) INFORMATION FOR SEQ ID NO: 39:

( i ) SEQUENCE CHARACTERISTICS:
  ( A ) LENGTH: 84 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 39:

```
AACACCCTGT ACCTGCAGAT GAACGGCCTG CAAGCCGAGG TGAGCGCCAT CTACTACTGC         60
GCCCGCGACC CATACTACTT CAGC                                                84
```

( 2 ) INFORMATION FOR SEQ ID NO: 40:

( i ) SEQUENCE CHARACTERISTICS:
    ( A ) LENGTH: 60 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 40:

```
GTCACCAGGG TACCCTGGCC CCAGAAGTCG AAGTAGTGGC CGCTGAAGTA GTATGGGTCG         60
```

( 2 ) INFORMATION FOR SEQ ID NO: 41:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 41:

```
CTGTACCTGC AGATGAACGG CCTGCAAGCC GAGGTG                                   36
```

( 2 ) INFORMATION FOR SEQ ID NO: 42:

( i ) SEQUENCE CHARACTERISTICS:
    ( A ) LENGTH: 60 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 42:

```
GGGGAAGACG GATGGGCCCT TGGTGGAAGC GCTGCTCACG GTCACCAGGG TACCCTGGCC         60
```

( 2 ) INFORMATION FOR SEQ ID NO: 43:

( i ) SEQUENCE CHARACTERISTICS:
    ( A ) LENGTH: 102 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 43:

```
GCTGAATTCG CCGCCACCAT GGGCTGGAGC TGTATCATCC TCTTCTTAGT AGCAACAGCT         60
ACAGGTGTCC ACTCCCAGGT CAAACTGGTA CAAGCTGGAG GT                           102
```

( 2 ) INFORMATION FOR SEQ ID NO: 44:

( i ) SEQUENCE CHARACTERISTICS:
    ( A ) LENGTH: 102 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 44:

```
GCGTACTAGT TAATGATAAC CCAGAGACGA TGCAACTCAG TCGCAGAGAT CTTCCTGGCT         60
```

```
GTACGACGCC ACCTCCAGCT TGTACCAGTT TGACCTGGGA GT                                102
```

( 2 ) INFORMATION FOR SEQ ID NO: 45:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 45:

```
GTCAGACTAG TAATAGTGTG AACTGGATAC GGCAAGCACC TGGCAAGGGT CTGGAGTGGG        60

TTGCACTAAT ATGGAGTAAT GGAGAC                                             86
```

( 2 ) INFORMATION FOR SEQ ID NO: 46:

( i ) SEQUENCE CHARACTERISTICS:
        ( A ) LENGTH: 73 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 46:

```
GTACTCTAGA GATTGTGAAT CGAGATTTGA TAGCTGAATT ATAATCTGTG TCTCCATTAC        60

TCCATATTAG TGC                                                           73
```

( 2 ) INFORMATION FOR SEQ ID NO: 47:

( i ) SEQUENCE CHARACTERISTICS:
        ( A ) LENGTH: 104 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 47:

```
GCAGAATTCT AGAGACAATT CGAAGAGCAC CCTATACATG CAGATGAACA GTCTGAGAAC        60

TGAAGATACT GCAGTCTACT TCTGTGCTCG TGAGTACTAT GGAT                        104
```

( 2 ) INFORMATION FOR SEQ ID NO:48:

( i ) SEQUENCE CHARACTERISTICS:
        ( A ) LENGTH: 99 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 48:

```
CTCGTGAGCT CGGGCCCTTG GTCGACGCTG AGGAGACTGT GACTAGGACA CCTTGACCCC        60

AATAGTCGAA ATATCCATAG TACTCACGAG CACAGAAGT                               99
```

( 2 ) INFORMATION FOR SEQ ID NO: 49:

( i ) SEQUENCE CHARACTERISTICS:
        ( A ) LENGTH: 70 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 49:

```
GCATCGCGTC GACCAAAGGT CCATCTGTGT TTCCGCTGGC GCCATGCTCC AGGAGCACCT        60

CCGAGAGCAC                                                               70
```

( 2 ) INFORMATION FOR SEQ ID NO: 50:

( i ) SEQUENCE CHARACTERISTICS:
    ( A ) LENGTH: 79 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 50:

```
GACAGAATTC AGGTGCTGGA CACGACGGAC ATGGAGGACC ATACTTCGAC TCAACTCTCT      60
TGTCCACCTT GGTGTTGCT                                                   79
```

( 2 ) INFORMATION FOR SEQ ID NO: 51:

( i ) SEQUENCE CHARACTERISTICS:
        ( A ) LENGTH: 68 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 51:

```
ACTGGAATTC CTAGGTGGAC CATCAGTCTT CCTGTTTCCG CCTAAGCCCA AGGACACTCT      60
CATGATCT                                                               68
```

( 2 ) INFORMATION FOR SEQ ID NO: 52:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 52:

```
CAGGCTGTCG ACTCGAGGCT GACCTTTGGC TTTGGAGATG GTTTTCTCGA T               51
```

( 2 ) INFORMATION FOR SEQ ID NO: 53:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 53:

```
GTAAGCGTCG ACTCGAGAGC CACAGGTGTA CACCCTGC                              38
```

( 2 ) INFORMATION FOR SEQ ID NO: 54:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 54:

```
CGCTAGCGGC CGCTCATTTA CCCAGAGACA GGGAGAGGCT                            40
```

( 2 ) INFORMATION FOR SEQ ID NO: 55:

( i ) SEQUENCE CHARACTERISTICS:
        ( A ) LENGTH: 76 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 55:

```
GATCCCTGCG CCTGAGCTGC GCCGCTAGCG GCTTCAGCTT CCGCAGCTAC GCCATGAGCT      60
GGGTGCGCCA GGCCCC                                                      76
```

( 2 ) INFORMATION FOR SEQ ID NO: 56:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 56:

```
GGGGCCTGGC GCACCCAGCT CATGGCGTAG CTGCGGAAGC TGAAGCCGCT AGCGGCGCAG      60

CTCAGGCGCA GG                                                          72
```

( 2 ) INFORMATION FOR SEQ ID NO: 57:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 57:

```
CTAGCGGCTT CACCTTCAGC AGCTACTGGA TGACCTGGGT GCGCCAGGCC CC              52
```

( 2 ) INFORMATION FOR SEQ ID NO: 58:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 58:

```
GGGGCCTGGC GCACCCAGGT CATCCAGTAG CTGCTGAAGG TGAAGCCG                   48
```

( 2 ) INFORMATION FOR SEQ ID NO: 59:

( i ) SEQUENCE CHARACTERISTICS:
        ( A ) LENGTH: 100 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 59:

```
CCAGCATCAG CATCAGCGGC GACAACACCT ACTACCCAGA CAGCGTGAAC GGCCGCTTCA      60

CCATCTCTAG AAACGACAGC AAGAACACCC TGTACCTGCA                            100
```

( 2 ) INFORMATION FOR SEQ ID NO: 60:

( i ) SEQUENCE CHARACTERISTICS:
        ( A ) LENGTH: 96 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 60:

```
GGTACAGGGT GTTCTTGCTG TCGTTTCTAG AGATGGTGAA GCGGCCGTTC ACGCTGTCTG      60

GGTAGTAGGT GTTGTCGCCG CTGATGCTGA TGCTGG                                96
```

( 2 ) INFORMATION FOR SEQ ID NO: 61:

( i ) SEQUENCE CHARACTERISTICS:
        ( A ) LENGTH: 123 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 61:

| | | | | | |
|---|---|---|---|---|---|
| AATTCGTCGA | CGCCGCCACC | ATGGGATGGA | GCTGTATCAT | CCTCTTCTTG | GTAGCAACAG | 60
| CTACAGGTGT | CCACTCCGAT | ATCCAGATGA | CCCAGAGCCC | ATCAAGCTTG | AGCGCGAGCG | 120
| TGG | | | | | | 123

( 2 ) INFORMATION FOR SEQ ID NO: 62:

( i ) SEQUENCE CHARACTERISTICS:
        ( A ) LENGTH: 124 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 62:

| | | | | | |
|---|---|---|---|---|---|
| GTCACCCACG | CTCGCGCTCA | AGCTTGATGG | GCTCTGGGTC | ATCTGGATAT | CGGAGTGGAC | 60
| ACCTGTAGCT | GTTGCTACCA | AGAAGAGGAT | GATACAGCTC | CATCCCATGG | TGGCGGCGTC | 120
| GACG | | | | | | 124

( 2 ) INFORMATION FOR SEQ ID NO: 63:

( i ) SEQUENCE CHARACTERISTICS:
        ( A ) LENGTH: 70 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 63:

| | | | | | |
|---|---|---|---|---|---|
| CAGCAGAAGC | CAGGCAAGGC | CCCAAAGCTG | CTGATCTACA | ACGCCAAGAG | CCTCGAGACC | 60
| GGCGTGCCAT | | | | | | 70

( 2 ) INFORMATION FOR SEQ ID NO: 64:

( i ) SEQUENCE CHARACTERISTICS:
        ( A ) LENGTH: 78 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 64:

| | | | | | |
|---|---|---|---|---|---|
| CTAGATGGCA | CGCCGGTCTC | GAGGCTCTTG | GCGTTGTAGA | TCAGCAGCTT | TGGGGCCTTG | 60
| CCTGGCTTCT | GCTGGTAC | | | | | 78

( 2 ) INFORMATION FOR SEQ ID NO: 65:

( i ) SEQUENCE CHARACTERISTICS:
        ( A ) LENGTH: 58 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 65:

| | | | | | |
|---|---|---|---|---|---|
| CTAGATTCAG | CGGAAGCGGT | TCCGGCACCG | ACTTCACCCT | CACCATCAGC | AGCCTGCA | 58

( 2 ) INFORMATION FOR SEQ ID NO: 66:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 66:

(2) INFORMATION FOR SEQ ID NO: 67:

(i) SEQUENCE CHARACTERISTICS:
    (A) LENGTH: 66 base pairs
    (B) TYPE: nucleic acid
    (C) STRANDEDNESS: single
    (D) TOPOLOGY: linear (xi) SEQUENCE DESCRIPTION: SEQ ID NO: 67:

```
GCCAGAGGAC TTCGCTACGT ACTACTGCCA GCAGTACTAC AGCGGCTGGA CCTTTGGCCA     60

AGCATG                                                                66
```

(2) INFORMATION FOR SEQ ID NO: 68:

(i) SEQUENCE CHARACTERISTICS:
    (A) LENGTH: 66 base pairs
    (B) TYPE: nucleic acid
    (C) STRANDEDNESS: single
    (D) TOPOLOGY: linear (xi) SEQUENCE DESCRIPTION: SEQ ID NO: 68:

```
CTTGGCCAAA GGTCCAGCCG CTGTAGTACT GCTGGCAGTA GTACGTAGCG AAGTCCTCTG     60

GCTGCA                                                                66
```

(2) INFORMATION FOR SEQ ID NO: 69:

(i) SEQUENCE CHARACTERISTICS:
    (A) LENGTH: 38 base pairs
    (B) TYPE: nucleic acid
    (C) STRANDEDNESS: single
    (D) TOPOLOGY: linear (xi) SEQUENCE DESCRIPTION: SEQ ID NO: 69:

```
CAGTGCGCTT TATCTCCACT TTGGTGCCCT GGCCAAAG                             38
```

(2) INFORMATION FOR SEQ ID NO: 70:

(i) SEQUENCE CHARACTERISTICS:
    (A) LENGTH: 393 base pairs
    (B) TYPE: nucleic acid
    (C) STRANDEDNESS: double
    (D) TOPOLOGY: linear (xi) SEQUENCE DESCRIPTION: SEQ ID NO: 70:

```
GAATTCGCCG CCACC ATG GGA TGG AGC TGT ATC ATC CTC TTC TTG GTA          48
                 Met Gly Trp Ser Cys Ile Ile Leu Phe Leu Val
                     -15                         -10

GCA ACA GCT ACA GGT GTC CAC TCC GAT ATC CAG ATG ACC CAG AGC CCA       96
Ala Thr Ala Thr Gly Val His Ser Asp Ile Gln Met Thr Gln Ser Pro
        -5            1                    5

TCA AGC TTG AGC GCG AGC GTG GGT GAC CGC GTG ACC ATC ACC TGC AAG       144
Ser Ser Leu Ser Ala Ser Val Gly Asp Arg Val Thr Ile Thr Cys Lys
        10              15                      20

GCC AGC CAG AAC ATC TAC AAG AAC CTG GCC TGG TAC CAG CAG AAG CCA       192
Ala Ser Gln Asn Ile Tyr Lys Asn Leu Ala Trp Tyr Gln Gln Lys Pro
25              30                      35                  40

GGC AAG GCC CCA AAG CTG CTG ATC TAC AAC GCC AAG AGC CTC GAG ACC       240
Gly Lys Ala Pro Lys Leu Leu Ile Tyr Asn Ala Lys Ser Leu Glu Thr
                45                  50                  55

GGC GTG CCA TCT AGA TTC AGC GGA AGC GGT TCC GGC ACC GAC CTC ACC       288
Gly Val Pro Ser Arg Phe Ser Gly Ser Gly Ser Gly Thr Asp Leu Thr
                60                  65                  70
```

| | | | | | | | | | | | | | | | | |
|---|---|---|---|---|---|---|---|---|---|---|---|---|---|---|---|---|
| TTC | ACC | ATC | AGC | AGC | CTG | CAG | CCA | GAG | GAC | TTC | GCT | ACG | TAC | TAC | TGC | 336 |
| Phe | Thr | Ile | Ser | Ser | Leu | Gln | Pro | Glu | Asp | Phe | Ala | Thr | Tyr | Tyr | Cys | |
| | | 75 | | | | | 80 | | | | | 85 | | | | |
| CAG | CAG | TAC | TAC | AGC | GGC | TGG | ACC | TTT | GGC | CAG | GGC | ACC | AAA | GTG | GAG | 384 |
| Gln | Gln | Tyr | Tyr | Ser | Gly | Trp | Thr | Phe | Gly | Gln | Gly | Thr | Lys | Val | Glu | |
| | 90 | | | | | 95 | | | | | 100 | | | | | |
| ATA | AAG | CGC | | | | | | | | | | | | | | 393 |
| Ile | Lys | Arg | | | | | | | | | | | | | | |
| 105 | | | | | | | | | | | | | | | | |

( 2 ) INFORMATION FOR SEQ ID NO: 71:

( i ) SEQUENCE CHARACTERISTICS:
        ( A ) LENGTH: 100 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 71:

CCAGCATCAG CATCAGCGGC GACAACACCT ACTACCCAGA CAGCGTGCGC GGCCGCTTCA     60

CCATCTCTAG AGACGACAGC AAGAGCACCC TGTACCTGCA     100

( 2 ) INFORMATION FOR SEQ ID NO: 72:

( i ) SEQUENCE CHARACTERISTICS:
        ( A ) LENGTH: 96 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 72:

GGTACAGGGT GCTCTTGCTG TCGTCTCTAG AGATGGTGAA GCGGCCGCGC ACGCTGTCTG     60

GGTAGTAGGT GTTGTCGCCG CTGATGCTGA TGCTGG     96

( 2 ) INFORMATION FOR SEQ ID NO: 73:

( i ) SEQUENCE CHARACTERISTICS:
        ( A ) LENGTH: 120 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 73:

GGGTCGACGC CGCCACCATG GGATGGAGCT GTATCATCCT CTTCTTGGTA GCAACAGCTA     60

CAGGTGTCCA CTCCGAGGTG CAGCTGGTGG AGAGCGGCGG AGGCCTGGTG CAGCCAGGCG     120

( 2 ) INFORMATION FOR SEQ ID NO: 74:

( i ) SEQUENCE CHARACTERISTICS:
        ( A ) LENGTH: 126 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 74:

GATCCGCCTG GCTGCACCAG GCCTCCGCCG CTCTCCACCA GCTGCACCTC GGAGTGGACA     60

CCTGTAGCTG TTGCTACCAA GAAGAGGATG ATACAGCTCC ATCCCATGGT GGCGGCGTCG     120

ACCCGC     126

( 2 ) INFORMATION FOR SEQ ID NO: 75:

( i ) SEQUENCE CHARACTERISTICS:
        ( A ) LENGTH: 99 base pairs
        ( B ) TYPE: nucleic acid ( C ) STRANDEDNESS: single
( D ) TOPOLOGY: linear ( x i ) SEQUENCE DESCRIPTION: SEQ ID NO: 75:

GATGAACGGC CTGCAAGCCG AGGTGAGCGC CATCTACTAC TGCGTTCGCG ACCCATACTA        60

CTTCAGCGGC CACTACTTCG ACTTCTGGGG CCAGGGTAC        99

( 2 ) INFORMATION FOR SEQ ID NO: 76:

( i ) SEQUENCE CHARACTERISTICS:
        ( A ) LENGTH: 99 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 76:

CCTGGCCCCA GAAGTCGAAG TAGTGGCCGC TGAAGTAGTA TGGGTCGCGA ACGCAGTAGT        60

AGATGGCGCT CACCTCGGCT TGCAGGCCGT TCATCTGCA        99

( 2 ) INFORMATION FOR SEQ ID NO: 77:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 77:

GATGAACAGC CTGCGCGCCG AGGACACCGC GGTATACTAC TGCGTTCG        48

( 2 ) INFORMATION FOR SEQ ID NO: 78:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 78:

CGAACGCAGT AGTATACCGC GGTGTCCTCG GCGCGCAGGC TGTTCATCTG CA        52

( 2 ) INFORMATION FOR SEQ ID NO: 79:

( i ) SEQUENCE CHARACTERISTICS:
        ( A ) LENGTH: 435 base pairs
        ( B ) TYPE: nucleic acid
        ( C ) STRANDEDNESS: double
        ( D ) TOPOLOGY: linear ( x i ) SEQUENCE DESCRIPTION: SEQ ID NO: 79:

```
GTCGACGCCG CCACC ATG GGA TGG AGC TGT ATC ATC CTC TTC TTG GTA              48
                 Met Gly Trp Ser Cys Ile Ile Leu Phe Leu Val
                     -15                     -10

GCA ACA GCT ACA GGT GTC CAC TCC GAG GTG CAG CTG GTG GAG AGC GGC          96
Ala Thr Ala Thr Gly Val His Ser Glu Val Gln Leu Val Glu Ser Gly
            -5                 1               5

GGA GGC CTG GTG CAG CCA GGC GGA TCC CTG CGC CTG AGC TGC GCC GCC         144
Gly Gly Leu Val Gln Pro Gly Gly Ser Leu Arg Leu Ser Cys Ala Ala
    10              15                  20

AGC GGC TTC AGC TTC CGC AGC TAC TGG ATG ACC TGG GTG CGC CAG GCC         192
Ser Gly Phe Ser Phe Arg Ser Tyr Trp Met Thr Trp Val Arg Gln Ala
25              30                  35                  40

CCG GGC AAG GGC CTG GAG TGG GTG GCC AGC ATC AGC ATC AGC GGC GAC         240
Pro Gly Lys Gly Leu Glu Trp Val Ala Ser Ile Ser Ile Ser Gly Asp
                45                  50                  55
```

```
AAC  ACC  TAC  TAC  CCA  GAC  AGC  GTG  CGC  GGC  CGC  TTC  ACC  ATC  TCT  AGA         288
Asn  Thr  Tyr  Tyr  Pro  Asp  Ser  Val  Arg  Gly  Arg  Phe  Thr  Ile  Ser  Arg
               60                  65                            70

GAC  GAC  AGC  AAG  AGC  ACC  CTG  TAC  CTG  CAG  ATG  AAC  AGC  CTG  CGC  GCC         336
Asp  Asp  Ser  Lys  Ser  Thr  Leu  Tyr  Leu  Gln  Met  Asn  Ser  Leu  Arg  Ala
               75                  80                       85

GAG  GAC  ACC  GCG  GTA  TAC  TAC  TGC  GTT  CGC  GAC  CCA  TAC  TAC  TTC  AGC         384
Glu  Asp  Thr  Ala  Val  Tyr  Tyr  Cys  Val  Arg  Asp  Pro  Tyr  Tyr  Phe  Ser
          90                  95                       100

GGC  CAC  TAC  TTC  GAC  TTC  TGG  GGC  CAG  GGT  ACC  CTG  GTG  ACC  GTG  AGC         432
Gly  His  Tyr  Phe  Asp  Phe  Trp  Gly  Gln  Gly  Thr  Leu  Val  Thr  Val  Ser
105                       110                       115                       120

AGC                                                                                    435
Ser
```

( 2 ) INFORMATION FOR SEQ ID NO: 80:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( x i ) SEQUENCE DESCRIPTION: SEQ ID NO: 80:

Gly  Phe  Thr  Phe  Ser  Ala  Ser  Ala  Met  Ser
                    5                        10

( 2 ) INFORMATION FOR SEQ ID NO: 81:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( x i ) SEQUENCE DESCRIPTION: SEQ ID NO: 81:

Trp  Lys  Tyr  Glu  Asn  Gly  Asn  Asp  Lys  His  Tyr  Ala  Asp  Ser  Val  Asn
                    5                        10                       15

( 2 ) INFORMATION FOR SEQ ID NO: 82:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( x i ) SEQUENCE DESCRIPTION: SEQ ID NO: 82:

Asp  Ala  Gly  Pro  Tyr  Val  Ser  Pro  Thr  Phe  Phe  Ala  His
                    5                        10

( 2 ) INFORMATION FOR SEQ ID NO: 83:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( x i ) SEQUENCE DESCRIPTION: SEQ ID NO: 83:

Gly  Phe  Ser  Phe  Arg  Ser  Tyr  Trp  Met  Thr
                    5                        10

( 2 ) INFORMATION FOR SEQ ID NO: 84:

( i ) SEQUENCE CHARACTERISTICS:

(A) LENGTH: 16 amino acids
(B) TYPE: amino acid
(C) STRANDEDNESS: single
(D) TOPOLOGY: linear (xi) SEQUENCE DESCRIPTION: SEQ ID NO: 84:

Ser Ile Ser Ile Ser Gly Asp Asn Thr Tyr Tyr Pro Asp Ser Val Arg
                5                   10                  15

(2) INFORMATION FOR SEQ ID NO: 85:

(i) SEQUENCE CHARACTERISTICS:
(A) LENGTH: 12 amino acids
(B) TYPE: amino acid
(C) STRANDEDNESS: single
(D) TOPOLOGY: linear (xi) SEQUENCE DESCRIPTION: SEQ ID NO: 85:

Asp Pro Tyr Tyr Phe Ser Gly His Tyr Phe Asp Phe
              5                   10

(2) INFORMATION FOR SEQ ID NO: 86:

(i) SEQUENCE CHARACTERISTICS:
(A) LENGTH: 10 amino acids
(B) TYPE: amino acid
(C) STRANDEDNESS: single
(D) TOPOLOGY: linear (xi) SEQUENCE DESCRIPTION: SEQ ID NO: 86:

Gly Phe Ser Phe Arg Ser Tyr Ala Met Ser
              5                   10

(2) INFORMATION FOR SEQ ID NO: 87:

(i) SEQUENCE CHARACTERISTICS:
(A) LENGTH: 10 amino acids
(B) TYPE: amino acid
(C) STRANDEDNESS: single
(D) TOPOLOGY: linear (xi) SEQUENCE DESCRIPTION: SEQ ID NO: 87:

Gly Phe Thr Phe Ser Ser Tyr Trp Met Thr
              5                   10

(2) INFORMATION FOR SEQ ID NO: 88:

(i) SEQUENCE CHARACTERISTICS:
(A) LENGTH: 16 amino acids
(B) TYPE: amino acid
(C) STRANDEDNESS: single
(D) TOPOLOGY: linear (xi) SEQUENCE DESCRIPTION: SEQ ID NO: 88:

Ser Ile Ser Ile Ser Gly Asp Asn Thr Tyr Tyr Pro Asp Ser Val Asn
                5                   10                  15